United States Patent [19]

Edwards et al.

[11] Patent Number: 5,420,298
[45] Date of Patent: May 30, 1995

[54] PYRROLIDINE DERIVATIVES

[75] Inventors: Philip N. Edwards, Bramhall; Michael S. Large, Stoke-on-Trent, both of United Kingdom

[73] Assignees: Zeneca Limited, London, England; Zeneca Pharma S.A., Cergy Cedex, France

[21] Appl. No.: 114,187

[22] Filed: Sep. 1, 1993

[30] Foreign Application Priority Data

Sep. 1, 1992 [EP] European Pat. Off. ............ 92402382
Jul. 6, 1993 [EP] European Pat. Off. ............ 93401752

[51] Int. Cl.$^6$ ................. C07D 207/12; C07D 207/14; C07D 207/06
[52] U.S. Cl. .................................. 548/556; 548/551; 548/571
[58] Field of Search ................ 548/556, 551, 571; 514/424

[56] References Cited

U.S. PATENT DOCUMENTS

| | | | |
|---|---|---|---|
| 3,083,208 | 3/1963 | Wu | 548/526 |
| 3,127,415 | 3/1964 | Wu | 260/326.5 |
| 4,567,184 | 1/1986 | Musser et al. | 514/277 |
| 4,625,034 | 11/1986 | Weiss et al. | 546/152 |
| 4,631,287 | 12/1986 | Chakraborty et al. | 514/307 |
| 4,725,619 | 2/1988 | Chakraborty et al. | 514/442 |
| 4,728,668 | 3/1988 | Chakraborty et al. | 514/464 |
| 4,794,188 | 12/1988 | Musser et al. | 546/152 |
| 4,839,369 | 6/1989 | Youssefyeh et al. | 514/314 |
| 4,868,193 | 9/1989 | Lee | 514/314 |
| 4,874,769 | 10/1989 | Youssefyeh et al. | 514/314 |
| 5,098,930 | 3/1992 | Edwards et al. | 514/460 |
| 5,098,932 | 3/1992 | Hamon | 514/462 |
| 5,105,020 | 4/1992 | Girodeau | 568/633 |
| 5,134,148 | 7/1992 | Crawley et al. | 514/312 |
| 5,137,913 | 8/1992 | Bird et al. | 514/467 |
| 5,179,115 | 1/1993 | Bruneau et al. | 514/387 |
| 5,196,419 | 3/1993 | Crawley et al. | 514/241 |
| 5,208,259 | 5/1993 | Bird et al. | 514/460 |
| 5,214,070 | 5/1993 | Bird et al. | 514/708 |
| 5,217,969 | 6/1993 | Bruneau et al. | 514/230.5 |
| 5,217,977 | 6/1993 | Crawley et al. | 514/311 |
| 5,217,978 | 6/1993 | Bird | 514/312 |

(List continued on next page.)

FOREIGN PATENT DOCUMENTS 0110405 6/1984 European Pat. Off. .

(List continued on next page.)

OTHER PUBLICATIONS

Wu et al, Chemical Abstracts 57: 12412A (1962).

(List continued on next page.)

Primary Examiner—C. Warren Ivy
Assistant Examiner—D. Margaret M. Mach
Attorney, Agent, or Firm—Cushman Darby & Cushman

[57] ABSTRACT

The invention concerns pyrrolidine derivatives of the formula

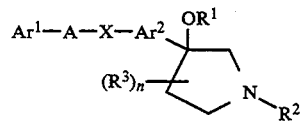

wherein $Ar^1$ is optionally-substituted phenyl, naphthyl or a 10-membered bicyclic heterocyclic moiety containing one or two nitrogen heteroatoms and optionally containing a further heteroatom selected from nitrogen, oxygen and sulphur;

A is a direct link to the group X or A is (1-4C)alkylene;

X is oxy, thio, sulphinyl or sulphonyl;

$Ar^2$ is phenylene, pyridinediyl, pyrimidinediyl, thiophendiyl, furandiyl or thiazolediyl;

$R^1$ is (1-4C)alkyl, (3-4C)alkenyl or (3-4C)alkynyl;

$R^2$ is (1-4C)alkyl, (2-4C)alkenyl, (2-4C)alkynyl, halogeno-(1-4C)alkyl, halogeno-(2-4C)alkenyl, halogeno-(2-4C)alkynyl, (1-4C)alkoxy-(2-4C)alkyl, hydroxy-(2-4C)alkyl, cyano-(1-4C)alkyl, carboxy-(1-4C)alkyl, carbamoyl-(1-4C)alkyl, (1-4C)alkoxycarbonyl-(1-4C)alkyl, N-(1-4C)alkylcarbamoyl-(1-4C)alkyl or N,N-di-(1-4C)alkylcarbamoyl-(1-4C)alkyl; and n is 1 or 2 and each $R^3$ is independently hydrogen, hydroxy, (1-4C)alkyl or (1-4C)alkoxy;

or a pharmaceutically-acceptable salt thereof;

processes for their manufacture; pharmaceutical compositions containing them and their use as 5-lipoxygenase inhibitors.

13 Claims, No Drawings

U.S. PATENT DOCUMENTS

| | | | |
|---|---|---|---|
| 5,219,881 | 6/1993 | Hamon | 514/452 |
| 5,221,677 | 6/1993 | Crawley et al. | 514/309 |
| 5,225,438 | 7/1993 | Dowell et al. | 514/459 |
| 5,234,950 | 8/1993 | Edwards et al. | 514/473 |
| 5,236,919 | 8/1993 | Crawley et al. | 514/349 |
| 5,236,948 | 8/1993 | Waterson | 514/459 |
| 5,240,941 | 8/1993 | Bruneau | 514/312 |

FOREIGN PATENT DOCUMENTS

| | | |
|---|---|---|
| 0181568 | 5/1986 | European Pat. Off. |
| 0190722 | 8/1986 | European Pat. Off. |
| 0200101 | 12/1986 | European Pat. Off. |

OTHER PUBLICATIONS

Mead Johnson, Chemical Abstracts 57: 16566a (1961).

Wu et al, Chemical Abstracts 59: 8709b (1963).

Review, Leukotriene research making prohress, Scripp No. 1613, May 3rd 1991 pp. 25–27.

Laursen et al., Selective 5-lipoxygenase inhibition in ulcerative colitis, The Lancet, vol. 335, pp. 683–685, Mar. 1990.

PYRROLIDINE DERIVATIVES

This invention concerns pyrrolidine derivatives and more particularly N-alkylpyrrolidine derivatives which are inhibitors of the enzyme 5-lipoxygenase (hereinafter referred to as 5-LO). The invention also concerns processes for the manufacture of said pyrrolidine derivatives and novel pharmaceutical compositions containing them. Also included in the invention is the use of said pyrrolidine derivatives in the treatment of various inflammatory and/or allergic diseases in which the direct or indirect products of 5-LO catalysed oxidation of arachidonic acid are involved, and the production of new medicaments for such use.

As stated above the pyrrolidine derivatives described hereinafter are inhibitors of 5-LO, which enzyme is known to be involved in catalysing the oxidation of arachidonic acid to give rise via a cascade process to the physiologically active leukotrienes such as leukotriene $B_4$ ($LTB_4$) and the peptido-lipid leukotrienes such as leukotriene $C_4$ ($LTC_4$) and leukotriene $D_4$ ($LTD_4$) and various metabolites.

The biosynthetic relationship and physiological properties of the leukotrienes are summarised by G. W. Taylor and S. R. Clarke in *Trends in Pharmacological Sciences*, 1986, 7, 100-103. The leukotrienes and their metabolites have been implicated in the production and development of various inflammatory and allergic diseases such as inflammation of the joints (especially rheumatoid arthritis, osteoarthritis and gout), inflammation of the gastrointestinal tract (especially inflammatory bowel disease, ulcerative colitis and gastritis), skin disease (especially psoriasis, eczema and dermatitis) and respiratory disease (especially asthma, bronchitis and allergic rhinitis), and in the production and development of various cardiovascular and cerebrovascular disorders such as myocardial infarction, angina and peripheral vascular disease. In addition the leukotrienes are mediators of inflammatory diseases by virtue of their ability to modulate lymphocyte and leukocyte function. Other physiologically active metabolites of arachidonic acid, such as the prostaglandins and thromboxanes, arise via the action of the enzyme cyclooxygenase on arachidonic acid.

It is disclosed in European Patent Application Nos. 0375404 and 0385662 that certain heterocyclic derivatives possess inhibitory properties against 5-LO. Furthermore European Patent Applications Nos. 0409413, 0420511, 0462812, 0462813, 0466452 and 0488602 are also concerned with heterocyclic derivatives which possess inhibitory properties against 5-LO. We have now discovered that certain pyrrolidine derivatives, which possess some structural features which are similar to those of the compounds disclosed in the above-mentioned applications but which possess other structural features in particular an N-alkylpyrrolidine group which was not specifically envisaged in those earlier applications, are effective inhibitors of the enzyme 5-LO and thus of leukotriene biosyntheses. Thus such compounds are of value as therapeutic agents in the treatment of, for example, allergic conditions, psoriasis, asthma, cardiovascular and cerebrovascular disorders, and/or inflammatory and arthritic conditions, mediated alone or in part by one or more leukotrienes.

According to the invention there is provided a pyrrolidine derivative of the formula I (set out hereinafter) wherein $Ar^1$ is phenyl or naphthyl, or a 10-membered bicyclic heterocyclic moiety containing one or two nitrogen heteroatoms and optionally containing a further heteroatom selected from nitrogen, oxygen and sulphur, and $Ar^1$ may optionally bear up to four substituents selected from halogeno, hydroxy, amino, cyano, formyl, oxo, thioxo, (1-4C)alkyl, (1-4C)alkoxy, fluoro-(1-4C)alkyl, hydroxy-(1-4C)alkyl, (2-4C)alkanoyl, (2-4C)alkanoylamino, $\underline{N}$-(1-4C)alkyl-(2-4C)alkanoylamino, hydroxyimino-(1-4C)alkyl, (1-4C)alkoxyimino-(1-4C)alkyl, (2-5C)alkanoyloxyimino-(1-4C)alkyl, cyano-(1-4C)alkoxyimino-(1-4C)alkyl, hydroxyamino-(1-4C)alkyl, (1-4C)alkoxyamino-(1-4C)alkyl, $\underline{N}$-hydroxyureido-(1-4C)alkyl, $\underline{N}$-(1-4C)alkoxyureido-(1-4C)alkyl, $\underline{N}$-hydroxy-(2-4C)alkanoylamino-(1-4C)alkyl, $\underline{N}$-(1-4C)alkoxy-(2-4C)alkanoylamino-(1-4C)alkyl, (1-6C)alkylideneaminooxy-(1-4C)alkyl, (1-4C)alkanesulphonamido, $\underline{N}$-(1-4C)alkyl-(1-4C)alkanesulphonamido, $\underline{N}$-(1-4C)alkylsulphamoyl, $\underline{N},\underline{N}$-di-(1-4C)alkylsulphamoyl, phenyl, benzoyl, benzyl, $\underline{N}$-phenylsulphamoyl and $\underline{N}$-(1-4C)alkyl-$\underline{N}$-phenylsulphamoyl, and wherein said phenyl substituent or any of said substituents which contains a phenyl group may optionally bear a substituent selected from halogeno, (1-4C)alkyl and (1-4C)alkoxy;

A is a direct link to the group X or A is (1-4C)alkylene;
X is oxy, thio, sulphinyl or sulphonyl;
$Ar^2$ is phenylene, pyridinediyl, pyrimidinediyl, thiophendiyl, furandiyl or thiazolediyl which may optionally bear one or two substituents selected from halogeno, cyano, trifluoromethyl, hydroxy, amino, (1-4C)alkyl, (1-4C)alkoxy, (1-4C)alkylamino and di-(1-4C)alkylamino;
$R^1$ is (1-4C)alkyl, (3-4C)alkenyl or (3-4C)alkynyl;
$R^2$ is (1-4C)alkyl, (2-4C)alkenyl, (2-4C)alkynyl, halogeno-(1-4C)alkyl, halogeno-(2-4C)alkenyl, halogeno-(2-4C)alkynyl, (1-4C)alkoxy-(2-4C)alkyl, hydroxy-(2-4C)alkyl, cyano-(1-4C)alkyl, carboxy-(1-4C)alkyl, carbamoyl-(1-4C)alkyl, (1-4C)alkoxycarbonyl-(1-4C)alkyl, $\underline{N}$-(1-4C)alkylcarbamoyl-(1-4C)alkyl or $\underline{N},\underline{N}$-di-(1-4C)alkylcarbamoyl-(1-4C)alkyl; and
n is 1 or 2 and each $R^3$ is independently hydrogen, hydroxy, (1-4C)alkyl or (1-4C)alkoxy;
or a pharmaceutically-acceptable salt thereof.

According to a further aspect of the invention there is provided a pyrrolidine derivative of the formula I as defined hereinbefore wherein $R^1$ may in addition be hydrogen; or a pharmaceutically-acceptable salt thereof.

According to another aspect of the invention there is provided a pyrrolidine derivative of the formula I wherein $Ar^1$ is phenyl which bears a substituent selected from hydroxyimino-(1-4C)alkyl, (1-4C)alkoxyimino-(1-4C)alkyl, (2-5C)alkanoyloxyimino-(1-4C)alkyl, cyano-(1-4C)alkoxyimino-(1-4C)alkyl, hydroxyamino-(1-4C)alkyl, (1-4C)alkoxyamino-(1-4C)alkyl, $\underline{N}$-hydroxyureido-(1-4C)alkyl, $\underline{N}$-(1-4C)alkoxyureido-(1-4C)alkyl, $\underline{N}$-hydroxy-(2-4C)alkanoylamino-(1-4C)alkyl, $\underline{N}$-(1-4C)alkoxy-(2-4C)alkanoylamino-(1-4C)alkyl and (1-6C)alkylideneaminooxy-(1-4C)alkyl, and $Ar^1$ may optionally bear a further substituent selected from halogeno, (1-4C)alkyl and (1-4C)alkoxy;
A is a direct link to the group X or A is (1-4C)alkylene;
X is oxy, thio, sulphinyl or sulphonyl;
$Ar^2$ is phenylene, pyridinediyl, pyrimidinediyl, thiophendiyl, furandiyl or thiazolediyl which may optionally bear one or two substituents selected from halogeno, cyano, trifluoromethyl, hydroxy, amino, (1-4C)alkyl, (1-4C)alkoxy, (1-4C)alkylamino and di-(1-4C)alkylamino;

$R^1$ is hydrogen, (1-4C)alkyl, (3-4C)alkenyl or (3-4C)alkynyl;

$R^2$ is (1-4C)alkyl, (2-4C)alkenyl, (2-4C)alkynyl, halogeno-(1-4C)alkyl, halogeno-(2-4C)alkenyl, halogeno-(2-4C)alkynyl, (1-4C)alkoxy-(2-4C)alkyl, hydroxy-(2-4C)alkyl, cyano-(1-4C)alkyl, carboxy-(1-4C)alkyl, carbamoyl-(1-4C)alkyl, (1-4C)alkoxycarbonyl-(1-4C)alkyl, N-(1-4C)alkylcarbamoyl-(1-4C)alkyl or N,N-di-(1-4C)alkylcarbamoyl-(1-4C)alkyl; and n is 1 or 2 and each $R^3$ is independently hydrogen, hydroxy, (1-4C)alkyl or (1-4C)alkoxy;

or a pharmaceutically-acceptable salt thereof.

The chemical formulae referred to herein by Roman numerals are set out for convenience on a separate sheet hereinafter.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of the formula I defined above may exhibit the phenomenon of tautomerism and any formula drawing presented herein may represent only one of the possible tautomeric forms, the invention includes in its definition any tautomeric form of a compound of the formula I which possesses the property of inhibiting 5-LO and is not to be limited merely to any one tautomeric form utilised within the formulae drawings.

It is further to be understood that, insofar as certain of the compounds of the formula I defined above are oxime derivatives and it is well known that oxime derivatives may exist in different geometric isomeric forms, commonly designated as (E)- or (Z)-isomers, the invention includes in its definition any such geometric isomeric form or a mixture thereof which possesses the property of inhibiting 5-LO. The separation of such geometric isomeric forms may be possible by the standard laboratory techniques of organic chemistry such as by chromatographic separation of a mixture of said isomeric forms or by crystallisation of one such isomeric form from a mixture thereof.

It is further to be understood that, insofar as certain of the compounds of formula I defined above may exist in optically active or racemic forms by virtue of one or more asymmetric carbon atoms, the invention includes in its definition any such optically active or racemic form which possesses the property of inhibiting 5-LO. The synthesis of optically active forms may be carried out by standard techniques of organic chemistry well known in the art, for example by synthesis from optically active starting materials or by resolution of a racemic form.

Suitable values for the generic terms referred to above include those set out below.

A suitable value for $Ar^1$ when it is naphthyl is, for example 1-naphthyl or 2-naphthyl.

A suitable value for $Ar^1$ when it is a 10-membered bicyclic heterocyclic moiety containing one or two nitrogen heteroatoms and optionally containing a further heteroatom selected from nitrogen, oxygen and sulphur is, for example, a 10-membered benzo-fused heterocyclic moiety such as quinolyl, isoquinolyl, cinnolinyl, quinazolinyl, quinoxalinyl, 4H-1,4-benzoxazinyl or 4H-1,4-benzothiazinyl, or a hydrogenated derivative thereof such as 1,2-dihydroquinolyl, 1,2,3,4-tetrahydroquinolyl, 1,2-dihydroisoquinolyl, 2,3-dihydro-4H-1,4-benzoxazinyl or 2,3-dihydro-4H-1,4-benzothiazinyl; or, for example, a 10-membered pyrido-fused heterocyclic moiety such as 1,7-naphthyridinyl, 1,8-naphthyridinyl, pyrido[2,3-d]pyrimidinyl, pyrido[2,3-b]pyrazinyl, 4H-pyrido[3,2-b][1,4]oxazinyl and 4H-pyrido[3,2-b][1,4]thiazinyl, or a hydrogenated derivative thereof.

The heterocyclic moiety may be attached through any available position including from either of the two rings of the bicyclic heterocyclic moiety and including through an available nitrogen atom. The heterocyclic moiety may bear a suitable substituent such as, for example, a (1-4C)alkyl, fluoro-(1-4C)alkyl, phenyl, benzoyl or benzyl substituent on an available nitrogen atom.

Suitable values for substituents which may be present on $Ar^1$, $Ar^2$ on or on any of the substituents on $Ar^1$ which contain a phenyl group include, for example:

for halogeno: fluoro, chloro, bromo and iodo;

for (1-4C)alkyl: methyl, ethyl, propyl, isopropyl, butyl, isobutyl, sec-butyl and tert-butyl;

for (1-4C)alkoxy: methoxy, ethoxy, propoxy, isopropoxy and butoxy;

for fluoro-(1-4C)alkyl: fluoromethyl, difluoromethyl, trifluoromethyl, 2-fluoroethyl, 2,2,2-trifluoroethyl and pentafluoroethyl;

for hydroxy-(1-4C)alkyl: hydroxymethyl, 1-hydroxyethyl, 2-hydroxyethyl and 3-hydroxypropyl;

for (2-4C)alkanoyl: acetyl, propionyl and butyryl;

for (2-4C)alkanoylamino: acetamido, propionamido and butyramido;

for N-(1-4C)alkyl-(2-4C)alkanoylamino: N-methylacetamido, N-ethylacetamido and N-methylpropionamido;

for hydroxyimino-(1-4C)alkyl: hydroxyiminomethyl, 1-hydroxyiminoethyl and 2-hydroxyiminoethyl;

for (1-4C)alkoxyimino(1-4C)alkyl: methoxyiminomethyl, ethoxyiminomethyl, 1-methoxyiminoethyl and 2-methoxyiminoethyl;

for (2-5C)alkanoyloxyimino(1-4C)alkyl: acetoxyiminomethyl, propionyloxyiminomethyl, 1-acetoxyiminoethyl and 2-acetoxyiminoethyl;

for cyano-(1-4C)alkoxyimino-(1-4C)alkyl: cyanomethoxyiminomethyl, 2-cyanoethoxyiminomethyl, 1-cyanomethoxyiminoethyl and 2-cyanomethoxyiminoethyl;

for hydroxyamino-(1-4C)alkyl: hydroxyaminomethyl, 1-hydroxyaminoethyl and 2-hydroxyaminoethyl;

for (1-4C)alkoxyamino(1-4C)alkyl: methoxyaminomethyl, ethoxyaminomethyl, 1-methoxyaminoethyl and 2-methoxyaminoethyl;

for N-hydroxyureido-(1-4C)alkyl: N-hydroxyureidomethyl, 1-(N-hydroxyureido)ethyl and 2-(N-hydroxyureido)ethyl;

for N-(1-4C)alkoxyureido(1-4C)alkyl: N-methoxyureidomethyl, N-ethoxyureidomethyl, 1-(N-methoxyureido)ethyl and 2-(N-methoxyureido)ethyl;

for N-hydroxy-(2-4C)alkanoyl-amino-(1-4C)alkyl: N-hydroxyacetamidomethyl, N-hydroxypropionamidomethyl, 1-(N-hydroxyacetamido)ethyl and 2-(N-hydroxyacetamido)ethyl;

for N-(1-4C)alkoxy-(2-4C)-alkanoylamino-(1-4C)alkyl: N-methoxyacetamidomethyl, N-ethoxyacetamidomethyl, 1-(N-methoxyacetamido)ethyl and 2-(N-methoxyacetamido)ethyl;

for (1-6C)alkylideneaminooxy(1-4C)alkyl: methyleneaminooxymethyl, ethylideneaminooxymethyl, isopropylideneamino-oxymethyl, 1-(isopropylideneaminooxy)ethyl and 2-(isopropylideneaminooxy)ethyl;

for (1-4C)alkanesulphonamido: methanesulphonamido and ethanesulphonamido;

for N-(1-4C)alkyl-(1-4C)alkanesulphonamido: N-methylmethanesulphonamido, N-ethylmethanesulphonamido and N-methylethanesulphonamido;

for N-(1-4C)alkylsulphamoyl: N-methylsulphamoyl, N-ethylsulphamoyl and N-propylsulphamoyl;

for N,N-di-(1-4C)alkylsulphamoyl: N,N-dimethylsulphamoyl, N-ethyl-N-methylsulphamoyl and N,N-diethylsulphamoyl;

for N-(1-4C)alkyl-N-phenylsulphamoyl: N-methyl-N-phenylsulphamoyl and N-ethyl-N-phenylsulphamoyl;

for (1-4C)alkylamino: methylamino, ethylamino, propylamino and isopropylamino; and for di-(1-4C)alkyamino: dimethylamino, N-ethyl-N-methylamino and diethylamino.

A suitable value for $Ar^2$ when it is phenylene is, for example, 1,3- or 1,4-phenylene.

A suitable value for A when it is (1-4C)alkylene is, for example, methylene, ethylene or trimethylene.

A suitable value for $Ar^2$ when it is pyridinediyl, pyrimidinediyl, thiophenediyl, furandiyl or thiazolediyl is, for example, 2,4-, 2,5- or 3,5-pyridinediyl, 4,6-pyrimidinediyl, 2,4- or 2,5-thiophenediyl, 2,4- or 2,5-furandiyl or 2,4- or 2,5-thiazolediyl.

A suitable value for $R^1$ when it is (1-4C)alkyl is, for example methyl, ethyl, propyl or butyl; when it is (3-4C)alkenyl is, for example allyl, 2-butenyl or 3-butenyl; and when it is (3-4C)alkynyl is, for example, 2-propynyl or 2-butynyl.

A suitable value for $R^2$ or $R^3$ when it is (1-4C)alkyl is, for example, methyl, ethyl, propyl, isopropyl or butyl.

A suitable value for $R^2$ when it is (2-4C)alkenyl is, for example, vinyl, allyl, 2-butenyl or 3-butenyl; when it is (2-4C)alkynyl is, for example, ethynyl, 2-propynyl or 2-butynyl; when it is halogeno-(1-4C)alkyl is, for example, fluoromethyl, difluoromethyl, trifluoromethyl, 2-fluoroethyl, 2,2-difluoroethyl, 2,2,2-trifluoroethyl, chloromethyl or 2-chloroethyl; when it is halogeno-(2-4C)alkenyl is, for example, 2-chlorovinyl, 2-chloroprop-2-enyl, 3-chloroprop-2-enyl, 2-chlorobut-2-enyl or 2-bromoprop-2-enyl; when it is halogeno-(2-4C)alkynyl is, for example 2-chloroethynyl or 3-chloroprop-2-ynyl; when it is (1-4C)alkoxy-(2-4C)alkyl is, for example, 2-methoxyethyl, 2-ethoxyethyl, 3-methoxypropyl or 3-ethoxypropyl; when it is hydroxy-(2-4C)alkyl is, for example, 2-hydroxyethyl or 3-hydroxypropyl; when it is cyano-(1-4C)alkyl is, for example, cyanomethyl, 2-cyanoethyl, 3-cyanopropyl or 2-cyanoprop-2-yl; when it is carboxy-(1-4C)alkyl is, for example, carboxymethyl, 2-carboxyethyl, 3-carboxypropyl or 2-carboxyprop-2-yl; when it is carbamoyl(1-4C)alkyl is, for example, carbamoylmethyl or 2-carbamoylethyl; when it is (1-4C)alkoxycarbonyl-(1-4C)alkyl is, for example, methoxycarbonylmethyl, ethoxycarbonylmethyl, 2-methoxycarbonylethyl, 3-methoxycarbonylpropyl or 2-methoxycarbonylprop-2-yl; when it is N-(1-4C)alkylcarbamoyl-(1-4C)alkyl is, for example, N-methylcarbamoylmethyl, N-ethylcarbamoylmethyl or 2-(N-methylcarbamoyl)ethyl; and when it is N,N-di-(1-4C)alkyl-carbamoyl-(1-4C)alkyl is, for example, N,N-dimethylcarbamoylmethyl, N-ethyl-N-methylcarbamoylmethyl, N,N-diethylcarbamoylmethyl or 2-(N,N-dimethylcarbamoyl)ethyl.

A suitable value for $R^3$ when it is (1-4C)alkoxy is, for example, methoxy, ethoxy or propoxy.

A suitable pharmaceutically-acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Particular compounds of the invention include, for example, pyrrolidine derivatives of the formula I, or pharmaceutically-acceptable salts thereof, wherein:

(a) $Ar^1$ is phenyl or naphthyl which may optionally bear one, two or three substituents selected from any of those substituents on $Ar^1$ defined hereinbefore other than oxo and thioxo; and A, X, $Ar^2$, $R^1$, $R^2$, $R^3$ and n have any of the meanings defined hereinbefore or in this section concerning particular compounds of the invention;

(b) $Ar^1$ is phenyl or naphth-2-yl which may optionally bear one or two substituents selected from fluoro, chloro, methyl, ethyl, isopropyl, tert-butyl, methoxy, trifluoromethyl, phenyl, benzoyl and benzyl, and wherein said phenyl, benzoyl or benzyl substituents may optionally bear a substituent selected from fluoro, chloro, methyl and methoxy; and A, X, $Ar^2$, $R^1$, $R^2$, $R^3$ and n have any of the meanings defined hereinbefore or in this section concerning particular compounds of the invention;

(c) $Ar^1$ is phenyl which bears one substituent selected from formyl, acetyl, propionyl, acetamido, propionamido, N-methylacetamido, N-ethylacetamido, hydroxyiminomethyl, 1-hydroxyiminoethyl, methoxyiminomethyl, ethoxyiminomethyl, 1-methoxyiminoethyl, 1-ethoxyiminoethyl, acetoxyiminomethyl, propionyloxyiminomethyl, 1-acetoxyiminoethyl, cyanomethoxyiminomethyl, 1-cyanomethoxyiminoethyl, methanesulphonamido, ethanesulphonamido, N-methylmethanesulphonamido, N-ethylmethanesulphonamido, N-methylsulphamoyl, N,N-dimethylsulphamoyl, phenyl, benzoyl, benzyl, N-phenylsulphamoyl and N-methyl-N-phenylsulphamoyl, and wherein said phenyl substituent or any of said substituents which contain a phenyl group may optionally bear one substituent selected from fluoro, chloro, methyl and methoxy, and $Ar^1$ may optionally bear a further substituent selected from fluoro, chloro, methyl, ethyl, methoxy, ethoxy and trifluoromethyl; and A, X, $Ar^2$, $R^1$, $R^2$, $R^3$ and n have any of the meanings defined hereinbefore or in this section concerning particular compounds of the invention;

(d) $Ar^1$ is phenyl which bears a substituent selected from hydroxyiminomethyl, 1-hydroxyiminoethyl, methoxyiminomethyl, ethoxyiminomethyl, 1-methoxyiminoethyl, 1-ethoxyiminoethyl, acetoxyiminomethyl, propionyloxyiminomethyl, 1-acetoxyiminoethyl, cyanomethoxyiminomethyl and 1-cyanomethoxyiminoethyl, and $Ar^1$ may optionally bear a further substituent selected from fluoro, chloro, methyl and methoxy; and A, X, $Ar^2$, $R^1$, $R^2$, $R^3$ and n have any of the meanings defined hereinbefore or in this section concerning particular compounds of the invention;

(e) $Ar^1$ is a 10-membered benzo-fused heterocyclic moiety containing one or two nitrogen heteroatoms and optionally containing a further heteroatom selected from oxygen and sulphur, which heterocyclic moiety may optionally bear one or two oxo or thioxo substituents and up to two further substituents selected from any of those substituents on $Ar^1$ defined hereinbefore other than oxo or thioxo; and A, X, $Ar^2$, $R^1$, $R^2$, $R^3$ and n have any of the meanings defined hereinbefore or in this section concerning particular compounds of the invention;

(f) $Ar^1$ is quinolyl, 1,2-dihydroquinolyl, 1,2,3,4-tetrahydroquinolyl or 2,3-dihydro-4H-1,4-benzoxazinyl which may optionally bear one oxo or thioxo substituent and up to two further substituents selected from fluoro, chloro, methyl, ethyl, methoxy, ethoxy, trifluoromethyl, acetyl, propionyl, phenyl, benzoyl and benzyl, and wherein each phenyl, benzoyl or benzyl substituent may optionally bear a substituent selected from fluoro, chloro, methyl and methoxy; and A, X, $Ar^2$, $R^1$, $R^2$, $R^3$ and n have any of the meanings defined hereinbefore or in this section concerning particular compounds of the invention;

(g) $Ar^1$ is 2-oxo-1,2-dihydroquinolinyl, 1-thioxo-1,2-dihydroquinolinyl, 2-oxo-1,2,3,4-tetrahydroquinolinyl, 2-thioxo-1,2,3,4-tetrahydroquinolinyl or 3-oxo-2,3-dihydro-4H-1,4-benzoxazinyl which may optionally bear up to three substituents selected from fluoro, chloro, methyl, ethyl, methoxy, ethoxy, trifluoromethyl, acetyl, propionyl, phenyl, benzoyl and benzyl, and wherein each phenyl, benzoyl or benzyl substituent may optionally bear a substituent selected from fluoro, chloro, methyl and methoxy; and A, X, $Ar^2$, $R^1$, $R^2$, $R^3$ and n have any of the meanings defined hereinbefore or in this section concerning particular compounds of the invention;

(h) $Ar^1$ is 2-oxo-1,2-dihydroquinolin-3-yl, 2-oxo-1,2-dihydroquinolin-6-yl, 2-oxo-1,2-dihydroquinolin-7-yl, 2-oxo-1,2,3,4-tetrahydroquinolin-6-yl or 3-oxo-2,3-dihydro-4H-1,4-benzoxazin-7-yl which may optionally bear up to three substituents selected from fluoro, chloro, methyl, ethyl, methoxy, ethoxy, trifluoromethyl, acetyl, propionyl, phenyl, benzoyl and benzyl, and wherein each phenyl, benzoyl or benzyl substituent may optionally bear a substituent selected from fluoro, chloro, methyl and methoxy; and A, X, $Ar^2$, $R^1$, $R^2$, $R^3$ and n have any of the meanings defined hereinbefore or in this section concerning particular compounds of the invention;

(i) $Ar^1$ is 2-oxo-1,2-dihydroquinolin-6-yl or 2-oxo-1,2,3,4-tetrahydroquinolin-6-yl which may optionally bear up to three substituents selected from fluoro, chloro, methyl, ethyl and trifluoromethyl; and A, X, $Ar^2$, $R^1$, $R^2$, $R^3$ and n have any of the meanings defined hereinbefore or in this section concerning particular compounds of the invention;

(j) A is a direct link to X; and $Ar^1$, X, $Ar^2$, $R^1$, $R^2$, $R^3$ and n have any of the meanings defined hereinbefore or in this section concerning particular compounds;

(k) A is (1-4C)alkylene and X is oxy; and $Ar^1$, $Ar^2$, $R^1$, $R^2$, $R^3$ and n have any of the meanings defined hereinbefore or in this section concerning particular compounds;

(l) A is a direct link to X and X is thio; and $Ar^1$, $Ar^2$, $R^1$, $R^2$, $R^3$ and n have any of the meanings defined hereinbefore or in this section concerning particular compounds;

(m) $Ar^2$ is phenylene which may optionally bear one or two substituents selected from halogeno, trifluoromethyl, amino (1-4C)alkyl and (1-4C)alkoxy, or $Ar^2$ is pyridinediyl, pyrimidinediyl or thiophenediyl; and $Ar^1$, A, X, $R^1$, $R^2$, $R^3$ and n have any of the meanings defined hereinbefore or in this section defining particular compounds;

(n) $R^1$ is (1-4C)alkyl; and $Ar^1$, A, X, $Ar^2$, $R^2$, $R^3$ and n have any of the meanings defined hereinbefore or in this section defining particular compounds;

(o) $R^2$ is (1-4C)alkyl, (2-4C)alkenyl, (2-4C)alkynyl, halogeno-(1-4C)alkyl, halogeno-(2-4C)alkenyl, cyano-(1-4C)alkyl, carboxy-(1-4C)alkyl, carbamoyl-(1-4C)alkyl or (1-4C)alkoxycarbonyl-(1-4C)alkyl; and $Ar^1$, A, X, $Ar^2$, $R^1$, $R^3$ and n have any of the meanings defined hereinbefore or in this section defining particular compounds;

(p) $R^2$ is (2-4C)alkenyl, (2-4C)alkynyl, halogeno-(1-4C)alkyl or halogeno-(2-4C)alkenyl; and $Ar^1$, A, X, $Ar^2$, $R^1$, $R^3$ and n have any of the meanings defined hereinbefore or in this section defining particular compounds;

(q) n is 1 and $R^3$ is hydrogen; and $Ar^1$ A, X, $Ar^2$, $R^1$ and $R^2$ have any of the meanings defined hereinbefore or in this section defining particular compounds; and (r) n is 1 and $R^2$ is (1-4C)alkyl; and $Ar^1$, A, X, $Ar^2$, $R^1$ and $R^2$ have any of the meanings defined hereinbefore or in this section defining particular compounds.

A further preferred compound of the invention comprises a pyrrolidine derivative of the formula I wherein $Ar^1$ is phenyl which may optionally bear one substituent selected from tert-butyl, acetyl, acetamido, $\underline{N}$-methylacetamido, 1-hydroxyiminoethyl,
1-methoxyiminoethyl, 1-cyanomethoxyiminoethyl, benzoyl and benzyl and wherein said benzoyl or benzyl substituents may optionally bear a fluoro group, or $Ar^1$ is naphth-2-yl which may optionally bear one substituent selected from fluoro, chloro, methyl, methoxy and trifluoromethyl, or $Ar^1$ is 2-oxo-1,2-dihydroquinolin-6-yl, 2-oxo-1,2,3,4-tetrahydroquinolin-6-yl or 3-oxo-2,3-dihydro-4H-1,4-benzoxazin-7-yl which may optionally bear one substituent selected from methyl and ethyl;

A is a direct link to X and X is thio, or A is methylene and X is oxy;

$Ar^2$ is 1,3-phenylene, 5-fluoro-1,3-phenylene, 2,5-thiophenediyl or 2,4-thiophenediyl (with the group of the formula -A-X- in the 2-position);

$R^1$ is methyl, ethyl or allyl;

$R^2$ is methyl, ethyl, propyl, allyl, prop-2-ynyl, 2,2,2-trifluoroethyl, 2-chloroprop-2-enyl, cyanomethyl, carbamoylmethyl, methoxycarbonylmethyl or ethoxycarbonylmethyl;

n is 1 and $R^3$ is hydrogen or methyl;

or a pharmaceutically-acceptable salt thereof.

A further preferred compound of the invention comprises a pyrrolidine derivative of the formula I wherein $Ar^1$ is phenyl which may optionally bear one substituent selected from tert-butyl, 1-hydroxyethyl, acetyl, acetamido, $\underline{N}$-methylacetamido, 1-hydroxyiminoethyl, 1- methoxyiminoethyl, 1-cyanomethoxyiminoethyl, benzoyl and benzyl and wherein said benzoyl or benzyl substituents may optionally bear a fluoro group.
or $Ar^1$ is naphth-2-yl which may optionally bear one substituent selected from fluoro, chloro, methyl, methoxy and trifluoromethyl, or $Ar^1$ is 2-oxo-1,2-dihydroquinolin-6-yl or 2-oxo-1,2,3,4-tetrahydroquinolin-6-yl which may optionally bear one substituent selected from methyl and ethyl;
A is a direct link to X and X is thio, sulphinyl or sulphonyl, or A is methylene and X is oxy;
$Ar^2$ is 1,3-phenylene, 5-fluoro-1,3-phenylene, 2,5-thiophenediyl or 2,4-thiophenediyl (with the group of the formula -A-X- in the 2-position);
$R^1$ is hydrogen, methyl, ethyl, allyl or prop-2-ynyl;
$R^2$ is methyl, ethyl, propyl, allyl, prop-2-ynyl, 2,2-difluoroethyl, 2,2,2-trifluoroethyl, 2-chloroprop-2-enyl, cyanomethyl, 2-cyanoethyl, carbamoylmethyl, methoxycarbonylmethyl or ethoxycarbonylmethyl;
n is 1 and $R^3$ is hydrogen or methyl;
or a pharmaceutically-acceptable salt thereof.

A further preferred compound of the invention comprises a pyrrolidine derivative of the formula I wherein $Ar^1$ is phenyl which bears one substituent selected from 1-hydroxyiminoethyl, 1-methoxyiminoethyl and 1-cyanomethoxyiminoethyl, and $Ar^1$ may optionally bear a further substituent selected from fluoro and chloro;
A is a direct link to X and X is thio, sulphinyl or sulphonyl, or A is methylene and X is oxy;
$Ar^2$ is 1,3-phenylene, 5-fluoro-1,3-phenylene, 2,5-thiophenediyl or 2,4-thiophenediyl (with the group of the formula -A-X- in the 2-position);
$R^1$ is hydrogen, methyl, ethyl, allyl or prop-2-ynyl;
$R^2$ is methyl, ethyl, propyl, allyl, prop-2-ynyl, 2,2-difluoroethyl, 2,2,2-trifluoroethyl, 2-chloroprop-2-enyl, cyanomethyl, 2-cyanoethyl, carbamoylmethyl, methoxycarbonylmethyl or ethoxycarbonylmethyl;
n is 1 and $R^3$ is hydrogen or methyl;
or a pharmaceutically-acceptable salt thereof.

A further preferred compound of the invention comprises a pyrrolidine derivative of the formula I wherein $Ar^1$ is naphth-2-yl which may optionally bear one substituent selected from fluoro, methyl and trifluoromethyl, or $Ar^1$ is 2-oxo-1,2-dihydroquinolin-6-yl or 2-oxo-1,2,3,4-tetrahydroquinolin-6-yl which may optionally bear a methyl or ethyl substituent;
A is methylene and X is oxy, or A is a direct link to X and X is thio or sulphonyl;
$Ar^2$ is 1,3-phenylene, 5-fluoro-1,3-phenylene, 2,5-thiophenediyl or 2,4-thiophenediyl (with the group of the formula -A-X- in the 2-position);
$R^1$ is methyl, ethyl, allyl or prop-2-ynyl;
$R^2$ is methyl, ethyl, propyl, allyl, prop-2-ynyl, 2,2-difluoroethyl, 2,2,2-trifluoroethyl, 2-chloroprop-2-enyl, cyanomethyl, 2-cyanoethyl or methoxycarbonylmethyl;
n is 1 and $R^3$ is hydrogen;
or a pharmaceutically-acceptable salt thereof.

A further preferred compound of the invention comprises a pyrrolidine derivative of the formula I wherein $Ar^1$ is naphth-2-yl or $Ar^1$ is 1-ethyl-2-oxo-1,2-dihydroquinolin-6-yl or 1-methyl-2-oxo-1,2-dihydroquinolin-6-yl;
A is methylene and X is oxy;
$Ar^2$ is 1,3-phenylene or 5-fluoro-1,3-phenylene;
$R^1$ is methyl;

$R^2$ is methyl, ethyl, prop-2-ynyl, 2,2,2-trifluoroethyl, 2-chloroprop-2-enyl, cyanomethyl or methoxycarbonylmethyl;
n is 1 and $R^3$ is hydrogen;
or a pharmaceutically-acceptable salt thereof.

A further preferred compound of the invention comprises a pyrrolidine derivative of the formula I wherein $Ar^1$ is 1-methyl-2-oxo-1,2-dihydroquinolin-6-yl, 1-ethyl-2-oxo-1,2-dihydroquinolin-6-yl or 1-methyl-2-oxo-1,2,3,4-tetrahydroquinolin-6-yl;
A is a direct link to X and X is thio or sulphonyl;
$Ar^2$ is 1,3-phenylene, 5-fluoro-1,3-phenylene, 2,5-thiophenediyl or 2,4-thiophenediyl (with the group of the formula -A-X- in the 2-position;
$R^1$ is methyl;
$R^2$ is prop-2-ynyl, 2,2-difluoroethyl or 2,2,2-trifluoroethyl;
n is 1 and $R^3$ is hydrogen;
or a pharmaceutically-acceptable salt thereof.

A further preferred compound of the invention comprises a pyrrolidine derivative of the formula I wherein $Ar^{-1}$ is 4-(1-hydroxyiminoethyl)phenyl or 4-(1-cyanomethoxyiminoethyl)phenyl;
A is a direct link to X and X is thio or sulphonyl;
Ar is 1,3-phenylene, 5-fluoro-1,3-phenylene, 2,5-thiophenediyl or 2,4-thiophenediyl (with the group of the formula -A-X- in the 2-position);
R is methyl;
$R^2$ is prop-2-ynyl, 2,2-difluoroethyl or 2,2,2-trifluoroethyl;
n is 1 and $R^3$ is hydrogen;
or a pharmaceutically-acceptable salt thereof.

A specific especially preferred compound of the invention is the following compound of the formula I:
3-methoxy-1-methyl-3-[3-(naphth-2-ylmethoxy)phenyl]pyrrolidine,
1-ethyl-3-methoxy-3-[3-(naphth-2-ylmethoxy)phenyl]pyrrolidine,
3-methoxy-3-[3-(naphth-2-ylmethoxy)phenyl]-1-(prop-2-ynyl)pyrrolidine,
1-cyanomethyl-3-methoxy-3-[3-(naphth-2-ylmethoxy)phenyl]pyrrolidine or
1-methoxycarbonylmethyl-3-methoxy-3-[3-(naphth-2-ylmethoxy)phenyl]pyrrolidine;
or a pharmaceutically-acceptable salt thereof.

A further specific especially preferred compound of the invention is the following compound of the formula I:
3-[3-(1-ethyl-2-oxo-1,2-dihydroquinolin-6-ylmethoxy)phenyl]-3-methoxy1-(2,2,2-trifluoroethyl)pyrrolidine,
3-methoxy-3-[3-(1-methyl-2-oxo-1,2-dihydroquinolin-6-ylmethoxy)phenyl]-1-(prop-2-ynyl)pyrrolidine,
3-[5-fluoro-3-(1-methyl-2-oxo-1,2,3,4-tetrahydroquinolin-6-ylthio)phenyl]-3-methoxy-1-(2,2,2-trifluoroethyl)pyrrolidine or
3-[5-fluoro-3-(1-methyl-2-oxo-1,2,3,4-tetrahydroquinolin-6-ylthio)phenyl]-1-(2,2-difluoroethyl)-3-methoxypyrrolidine;
or a pharmaceutically-acceptable salt thereof.

A further specific especially preferred compound of the invention is the following compound of the formula I:
3-[3-(4-acetylphenylthio)phenyl]-3-methoxy-1-(prop-2-ynyl)pyrrolidine,
3-[3-(4-acetylphenylthio)phenyl]-3-methoxy-1-(2,2,2-trifluoroethyl)pyrrolidine, 3-{5-fluoro-3-[4-(N-methylacetamido)phenylthio]-
  phenyl}-3-methoxy-1(2,2,2-trifluoroethyl)pyrrolidine
  or
3-[2-(4-acetylphenylthio)thien-4-yl]-3-methoxy-1-(2,2,2-
  trifluoroethyl)pyrrolidine;
or a pharmaceutically-acceptable salt thereof.

A further specific especially preferred compound of the invention is the following compound of the formula I:

3-{2-[4-(1-hydroxyiminoethyl)phenylthio]thien-4-yl}-3-methoxy-1-(2,2,2-trifluoroethyl)pyrrolidine,
3-{3-[4-(1-cyanomethoxyiminoethyl)phenylthio]-phenyl}-3-methoxy-1-(2,2,2-trifluoroethyl)pyrrolidine,
3-{5-fluoro-3-[4-(1-hydroxyiminoethyl)phenylthio]-phenyl}-3-methoxy-1-(prop-2-ynyl)pyrrolidine or
3-{5-fluoro-3-[4-(1-hydroxyiminoethyl)phenylthio]-phenyl}-3-methoxy-1-(2,2,2-trifluoroethyl)pyrrolidine;
or a pharmaceutically-acceptable salt thereof.

A compound of the invention comprising a pyrrolidine derivative of the formula I, or a pharmaceutically-acceptable salt thereof, may be prepared by any process known to be applicable to the preparation of structurally-related compounds. Suitable procedures are provided hereinafter as a further feature of the invention and are illustrated by the following representative examples in which, unless otherwise stated, $Ar^1$, A, X, $Ar^2$, $R^1$, $R^2$, $R^3$ and n have any of the meanings defined hereinbefore provided that when there is an amino, alkylamino, carboxy or hydroxy group in $Ar^1$, $Ar^2$, $R^2$ or $R^3$ then any such group may optionally be protected by a conventional protecting group which may be removed when so desired by conventional means.

(a) The alkylation, conveniently in the presence of a suitable base, of a compound of the formula II with a compound of the formula $Ar^1$-A-Z wherein Z is a displaceable group.

A suitable displaceable group Z is, for example, a halogeno or sulphonyloxy group, for example a fluoro, chloro, bromo, iodo, methanesulphonyloxy or toluene-4-sulphonyloxy group.

A suitable base for the reaction is, for example, an alkali or alkaline earth metal carbonate, (1-4C)alkoxide, (1-4C)alkanoate, hydroxide or hydride, for example sodium carbonate, potassium carbonate, sodium ethoxide, potassium butoxide, sodium acetate, lithium hydroxide, sodium hydroxide, potassium hydroxide, sodium hydride or potassium hydride. Alternatively a suitable base for the reaction is, for example, an organic amine base such as pyridine, 2,6-lutidine, collidine, 4-dimethylaminopyridine, triethylamine, diisopropylethylamine, N-methylmorpholine or diazabicyclo[5.4.0]undec-7-ene. The reaction is conveniently performed in a suitable inert solvent or diluent, for example N,N-dimethylformamide, N,N-dimethylacetamide, N-methylpyrrolidin-2-one, dimethylsulphoxide, acetonitrile, acetone, 1,2-dimethoxyethane or tetrahydrofuran, and at a temperature in the range, for example, 10° to 150° C., conveniently at or near ambient temperature.

The starting materials of the formula II may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist.

A suitable protecting group for an amino or alkylamino group is, for example, an acyl group for example a (2-4C)alkanoyl group (especially acetyl), a (1-4C)alkoxycarbonyl group (especially methoxycarbonyl, ethoxycarbonyl or tert-butoxycarbonyl), an arylmethoxycarbonyl group (especially benzyloxycarbonyl) or an aroyl group (especially benzoyl). The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-charcoal.

A suitable protecting group for a hydroxy group is, for example, an acyl group, for example a (2-4C)alkanoyl group (especially acetyl), an aroyl group (especially benzoyl) or an arylmethyl group (especially benzyl). The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group be removed, for example, by hydrogenation over a catalyst such as palladium-on-charcoal.

A suitable protecting group for a carboxy group is, for example, an esterifying group, for example a (1-4C)alkyl group (especially methyl or ethyl) or an arylmethyl group (especially benzyl). The deprotection conditions for the above protecting groups necessarily vary with the choice of protecting group. Thus, for example, an esterifying group such as an alkyl or arylmethyl group may be removed, for example, by hydrolysis with a suitable base such as an alkali metal hydroxide, for example lithium or sodium hydroxide. Alternatively an esterifying group such as an arylmethyl group may be removed, for example, by hydrogenation over a catalyst such as palladium-on-charcoal.

(b) The alkylation, conveniently in the presence of a suitable base as defined hereinbefore, of a compound of the formula III with a compound of the formula $R^1$-Z wherein Z is a displaceable group as defined hereinbefore.

The reaction is conveniently performed in a suitable inert solvent or diluent as defined hereinbefore and at a temperature in the range, for example, 10° to 150° C., conveniently at or near ambient temperature.

The starting materials of the formula III may be obtained by standard procedures of organic chemistry using analogous procedures to those illustrated in the accompanying Examples.

(c) The alkylation, conveniently in the presence of a suitable base as defined hereinbefore, of a compound of the formula IV with a compound of the formula $R^2$-Z wherein Z is a displaceable group as defined hereinbefore.

The reaction is conveniently performed in a suitable inert solvent or diluent as defined hereinbefore and at a temperature in the range, for example, 10° to 150° C., conveniently at or near ambient temperature.

The starting materials of the formula IV may be obtained by standard procedures of organic chemistry using analogous procedures to those illustrated in the accompanying Examples.

(d) For the production of those compounds of the formula I wherein $R^2$ is (1-4C)alkyl or halogeno-(1-4C)alkyl, the reduction of a compound of the formula V wherein R is a (1-4C)alkoxycarbonyl group, a (2-4C)alkanoyl group or a halogeno-(2-4C)alkanoyl group.

Any reducing agent known in the art for the reduction of an ester or alkanoyl group may be employed. A suitable reducing agent is, for example, a hydride reducing agent, for examples an alkali metal aluminium hydride such as lithium aluminium hydride or a borane-based hydride such as diborane, borane-pyridine complex, borane-trimethylamine complex, borane-tetrahydrofuran complex or borane-dimethyl sulphide complex.

The reduction is conveniently performed in a suitable inert solvent or diluent, for example, 1,2-dimethoxyethane, diethyl ether or tetrahydrofuran. A less powerful reducing agent such as borane-pyridine complex may be used in a protic solvent, for example, a (1-4C)alcohol such as methanol, ethanol and propanol. The reaction is conveniently performed at a temperature in the range, for example −10° to 100° C., conveniently at or near 60° C.

The starting materials of the formula V may be obtained by standard procedures of organic chemistry. The preparation of such starting materials is described within the accompanying non-limiting Examples.

(e) The coupling, conveniently in the presence of a suitable base as defined hereinbefore, of a compound of the formula $Ar^1$-A-X-H with a compound of the formula VI wherein Z is a displaceable group as defined hereinbefore.

Conveniently the reaction may be performed in the presence of a suitable catalyst, for example a metallic catalyst, for example palladium(O) or copper(I) such as tetrakis(triphenylphosphine)palladium, cuprous chloride or cuprous bromide.

The reaction is conveniently performed in a suitable inert solvent or diluent as defined hereinbefore and at a temperature in the range, for example, 10° to 180° C., conveniently at or near 120° C.

The starting materials of the formula VI may be obtained by standard procedures of organic chemistry using analogous procedures to those illustrated in the accompanying Examples.

(f) For the production of those compounds of the formula I wherein $Ar^1$ bears a hydroxyimino-(1-4C)alkyl substituent or an O-substituted hydroxyimino-(1-4C)alkyl substituent, the reaction of a compound of the formula I wherein Ar bears a formyl or (2-4C)alkanoyl substituent with hydroxylamine or an appropriate O-substituted hydroxylamine.

The reaction is conveniently performed in a suitable inert solvent or diluent, for example, one or more of water, a (1-4C)alcohol such as methanol, ethanol and propanol, pyridine, 1,2-dimethoxyethane, tetrahydrofuran, 1,4-dioxan or a dipolar aprotic solvent such as N,N-dimethylformamide and dimethylsulphoxide. The reaction is conveniently performed at a temperature in the range, for example, 10° to 150° C., conveniently at or near 70° C.

(g) For the production of those compounds of the formula I wherein $Ar^1$ bears a (1-4C)alkoxyimino-(1-4C)alkyl substituent or a cyano-(1-4C)alkoxyimino-(1-4C)alkyl substituent, the alkylation, conveniently in the presence of a suitable base as defined hereinbefore, of a compound of the formula I wherein $Ar^1$ bears a hydroxyimino-(1-4C)alkyl substituent with an alkylating agent of the formula R'-Z wherein R' is a (1-4C)alkyl group or a cyano-(1-4C)alkyl group and Z is a displaceable group as defined hereinbefore.

The reaction is conveniently performed in a suitable inert solvent or diluent, for example N,N-dimethylformamide, N,N-dimethylacetamide, dimethylsulphoxide, 1,2-dimethoxyethane, tetrahydrofuran or 1,4-dioxan, and at a temperature in the range, for example, −10° to 150° C., conveniently at or near ambient temperature.

(h) For the production of those compounds of the formula I wherein $Ar^1$ bears a N-(1-4C)alkyl-(2-4C)alkanoylamino substituent, the alkylation, conveniently in the presence of a suitable base as defined hereinbefore, of a compound of the formula I wherein $Ar^1$ bears a (2-4C)alkanoylamino substituent, with an alkylating agent of the formula R"-Z wherein R" is a (1-4C)alkyl group and Z is a displaceable group as defined hereinbefore.

The reaction is conveniently performed in a suitable inert solvent or diluent as defined hereinbefore and at a temperature in the range, for example, −10° to 150° C., conveniently at or near ambient temperature.

(i) For the production of those compounds of the formula I wherein X is a sulphinyl or sulphonyl group, the oxidation of a compound of the formula I wherein X is a thio group.

A suitable oxidising agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), a di-(1-4C)alkyldioxiran (such as dimethyldioxiran), chromium trioxide or gaseous oxygen in the presence of platinum. The oxidation is generally carried out under as mild conditions as possible and with the required stoichiometric amount of oxidising agent in order to reduce the risk of over oxidation and damage to other functional groups. In general the reaction is carried out in a suitable solvent or diluent such as methylene chloride, chloroform, acetone, tetrahydrofuran or tert-butyl methyl ether and at a temperature, for example, at or near ambient temperature, that is in the range 15° to 35° C. When a compound carrying a sulphinyl group is required a milder oxidising agent may also be used, for example sodium or potassium metaperiodate, conveniently in a polar solvent such as acetic acid or ethanol. It will be appreciated that when a compound of the formula I containing a sulphonyl group is required, it may be obtained by oxidation of the corresponding sulphinyl compound as well as of the corresponding thio compound.

When a pharmaceutically-acceptable salt of a compound of the formula I is required, it may be obtained, for example, by reaction of said compound with a suitable acid or base using a conventional procedure. When an optically active form of a compound of the formula I is required, it may be obtained by carrying out one of the aforesaid procedures using an optically active starting material, or by resolution of a racemic form of said compound using a conventional procedure.

As stated previously, the compounds of the formula I are inhibitors of the enzyme 5-LO. The effects of this inhibition may be demonstrated using one or more of the standard procedures set out below:

a) An in vitro assay system involving incubating a test compound with heparinised human blood, prior to challenge with the calcium ionophore A23187 and then indirectly measuring the inhibitory effects on 5-LO by assaying the amount of $LTB_4$ using specific radioimmunoassays described by Carey and Forder (F. Carey and R. A. Forder, *Prostaglandins, Leukotrienes Med.*, 1986, 22, 57; *Prostaglandins*, 1984, 28, 666; *Brit. J. Pharmacol.* 1985, 84, 34P) which involve the use of a protein-$LTB_4$ conjugate produced using the procedure of Young et alia (*Prostaglandins*, 1983, 26(4), 605–613). The effects of a test compound on the enzyme cyclooxygenase (which is involved in the alternative metabolic pathway for arachidonic acid and gives rise to prostaglandins, thromboxanes and related metabolites) may be measured at the same time using the specific radioimmunoassay for thromboxane $B_2(TxB_2)$ described by Carey and Forder (see above). This test provides an indication of the effects of a test compound against 5-LO and also cyclooxygenase in the presence of blood cells and proteins. It permits the selectivity of the inhibitory effect on 5-LO or cyclooxygenase to be assessed.

b) An ex vivo assay system, which is a variation of test a) above, involving administration to a group of rats of a test compound (usually orally as the suspension produced when a solution of the test compound in dimethylsulphoxide is added to carboxymethylcellulose), blood collection, heparinisation, challenge with A23187 and radioimmunoassay of $LTB_4$ and $TxB_2$. This test provides an indication of the bioavailability of a test compound as an inhibitor of 5-LO or cyclooxygenase.

c) An in vivo system involving measuring the effects of a test compound administered orally against the liberation of $LTB_4$ induced by zymosan within an air pouch generated within the subcutaneous tissue of the back of male rats. The rats are anaesthetised and air pouches are formed by the injection of sterile air (20 ml). A further injection of air (10 ml) is similarly given after 3 days. At 6 days after the initial air injection the test compound is administered (usually orally as the suspension produced when a solution of the test compound in dimethylsulphoxide is added to hydroxypropylmethylcellulose), followed by the intrapouch injection of zymosan (1 ml of a 1% suspension in physiological saline). After 3 hours the rats are killed, the air pouches are lavaged with physiological saline, and the specific radioimmunoassay described above is used to assay $LTB_4$ in the washings. This test provides an indication of inhibitory effects against 5-LO in an inflammatory milieu.

Although the pharmacological properties of the compounds of the formula I vary with structural changes as expected, in general compounds of the formula I possess 5-LO inhibitory effects at the following concentrations or doses in at least one of the above tests a)-c):

Test a): $IC_{50}$ ($LTB_4$) in the range, for example, 0.01–40 $IC_{50}$ ($TxB_2$) in the range, for example, 40–200

Test b): oral $ED_{50}(LTB_4)$ in the range, for example, 0.1–100 mg/kg;

Test c): oral $ED_{50}(LTB_4)$ in the range, for example, 0.1–100 mg/kg.

No overt toxicity or other untoward effects are present in tests b) and/or c) when compounds of the formula I are administered at several multiples of their minimum inhibitory dose or concentration.

Thus, by way of example, the compound:

3-methoxy-1-methyl-3-[3-(naphth-2-ylmethoxy)-phenyl]pyrrolidine has an $IC_{50}$ of 0.21 $\mu$M against $LTB_4$ in test (a);

3-methoxy-3-[3-(naphth-2-ylmethoxy)phenyl]-1-(prop-2-ynyl)pyrrolidine has an $IC_{50}$ of 0.06 $\mu$M against $LTB_4$ in test (a);

3-[3-(1-ethyl-2-oxo-1,2-dihydroquinolin-6-ylmethoxy)-phenyl]-3-methoxy-1-(2,2,2-trifluoroethyl)pyrrolidine has an $IC_{50}$ of 0.09 $\mu$M against $LTB_4$ in test (a);

3-[5-fluoro-3-(1-methyl-2-oxo-1,2,3,4-tetrahydroquinolin-6-ylthio)phenyl]-3-methoxy-1-(2,2,2-trifluoroethyl)pyrrolidine has an $IC_{50}$ of 0.03 $\mu$M against $LTB_4$ in test (a) and an $ED_{50}$ of approximately 1.5 mg/kg versus $LTB_4$ in test (c); and 3-{5-fluoro-3-[4-(1-hydroxyiminoethyl)phenylthio]-phenyl}-3-methoxy-1-(2,2,2-trifluoroethyl)pyrrolidine has an $IC_{50}$ of 0.04 $\mu$M against $LTB_4$ in test (a) and an $ED_{50}$ of approximately 0.5 mg/kg versus $LTB_4$ in test (c).

These compounds are examples of compounds of the invention which show selective inhibitory properties for 5-LO as opposed to cyclooxygenase, which selective properties are expected to impart improved therapeutic properties, for example, a reduction in or freedom from the gastrointestinal side-effects frequently associated with cyclooxygenase inhibitors such as indomethacin.

According to a further feature of the invention there is provided a pharmaceutical composition which comprises a pyrrolidine derivative of the formula I, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder such as a dry powder, a microcrystalline form or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general the above compositions may be prepared in a conventional manner using conventional excipients.

The amount of active ingredient (that is a pyrrolidine derivative of the formula I, or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

According to a further feature of the invention there is provided a pyrrolidine derivative of the formula I, or a pharmaceutically-acceptable salt thereof, for use in a method of treatment of the human or animal body by therapy.

The invention also includes a method of treating a disease or medical condition mediated alone or in part by one or more leukotrienes which comprises administering to a warm-blooded animal requiring such treatment an effective amount of an active ingredient as defined above. The invention also provides the use of such an active ingredient in the production of a new medicament for use in a leukotriene mediated disease or medical condition.

The size of the dose for therapeutic or prophylactic purposes of a compound of the formula I will naturally vary according to the nature and severity of the conditions, the age and sex of the animal or patient and the route of administration, according to well known principles of medicine. As mentioned above, compounds of the formula I are useful in treating those allergic and inflammatory conditions which are due alone or in part to the effects of the metabolites of arachidonic acid arising by the linear (5-LO catalysed) pathway and in particular the leukotrienes, the production of which is mediated by 5-LO. As previously mentioned, such conditions include, for example, asthmatic conditions, allergic reactions, allergic rhinitis, allergic shock, psoriasis, atopic dermatitis, cardiovascular and cerebrovascular disorders of an inflammatory nature, arthritic and inflammatory joint disease, and inflammatory bowel diseases.

In using a compound of the formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used.

Although the compounds of the formula I are primarily of value as therapeutic agents for use in warm-blooded animals (including man), they are also useful whenever it is required to inhibit the enzyme 5-LO. Thus, they are useful as pharmacological standards for use in the development of new biological tests and in the search for new pharmacological agents.

By virtue of their effects on leukotriene production, the compounds of the formula I have certain cytoprotective effects, for example they are useful in reducing or suppressing certain of the adverse gastrointestinal effects of the cyclooxygenase inhibitory nonsteroidal anti-inflammatory agents (NSAIA), such as indomethacin, acetylsalicylic acid, ibuprofen, sulindac, tolmetin and piroxicam. Furthermore, co-administration of a 5-LO inhibitor of the formula I with a NSAIA can result in a reduction in the quantity of the latter agent needed to produce a therapeutic effect, thereby reducing the likelihood of adverse side-effects. According to a further feature of the invention there is provided a pharmaceutical composition which comprises a pyrrolidine derivative of the formula I, or a pharmaceutically-acceptable salt thereof as defined hereinbefore, in conjunction or admixture with a cyclooxygenase inhibitory non-steroidal anti-inflammatory agent (such as those mentioned above), and a pharmaceutically-acceptable diluent or carrier.

The cytoprotective effects of the compounds of the formula I may be demonstrated, for example in a standard laboratory model which assesses protection against indomethacin-induced or ethanol-induced ulceration in the gastrointestinal tract of rats.

The compositions of the invention may in addition contain one or more therapeutic or prophylactic agents known to be of value for the disease under treatment. Thus, for example a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an anti-histamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

The invention will now be illustrated in the following non-limiting Examples in which, unless otherwise stated:

(i) evaporations were carried out by rotary evaporation in vacuo and work-up procedures were carried out after removal of residual solids by filtration;

(ii) operations were carried out at ambient temperature, that is in the range 18°–25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany;

(iv) yields are given for illustration only and are not necessarily the maximum attainable;

(v) the end-products of the formula I have satisfactory microanalyses and their structures were confirmed by nuclear magnetic resonance (NMR) and mass spectral techniques; unless otherwise stated, $CDCl_3$ solutions of the end-products of the formula I were used for the determination of NMR spectral data, chemical shift values were measured on the delta scale; the following abbreviations have been used: s, singlet; d, doublet; t, triplet; m, multiplet;

(vi) intermediates were not generally fully characterised and purity was assessed by thin layer chromatographic, infra-red (IR) or NMR analysis;

(vii) melting points are uncorrected and were determined using a Mettler SP62 automatic melting point apparatus or an oil-bath apparatus; melting points for the end-products of the formula I were determined after crystallisation from a conventional organic solvent such as ethanol, methanol, acetone, ether or hexane, alone or in admixture; and (viii) the following abbreviations have been used:

| THF | tetrahydrofuran; |
|---|---|
| DMF | N,N-dimethylformamide; |
| NMP | N-methylpyrrolidin-2-one; |
| DMSO | dimethylsulphoxide. |

EXAMPLE 1

Lithium aluminium hydride (1M in diethyl ether, 4 ml) was added dropwise to a stirred solution of 1-ethoxycarbonyl-3-methoxy-3-[3-(naphth-2-ylmethoxy)-phenyl]pyrrolidine (0.7 g) in THF (20 ml). The mixture was heated to reflux for 2 hours. The mixture was cooled to ambient temperature. Ethyl acetate (20 ml) and water (20 ml) were added dropwise in turn and the mixture was filtered. The filtrate was dried ($Na_2SO_4$) and evaporated. There was thus obtained 3-methoxy-1- methyl-3-[3-(naphth-2-ylmethoxy)phenyl]pyrrolidine (0.58 g, 97%) a solid, a portion of which was dissolved in diethyl ether and treated with hydrogen chloride gas. There was thus obtained the hydrochloride salt of the above-named pyrrolidine, m.p. 162°–164° C. (recrystallised from ethyl acetate).

NMR Spectrum (CD$_3$OD) 2.45–2.75 (m, 2H), 2.99 (s, 3H), 3.0 (s, 3H), 3.4–3.6 (m, 2H), 3.75 (m, 1H), 3.92 (m, 1H), 5.29 (s, 2H), 7.02 (m, 1H), 7.1 (m, 2H), 7.38 (m, 1H), 7.48 (m, 2H), 7.55 (m, 1H), 7.9 (m, 4H).

The 1-ethoxycarbonyl-3-methoxy-3-[3-(naphth-2-ylmethoxy)phenyl]pyrrolidine used as a starting material was obtained as follows:

n-Butyl-lithium (1.6M in hexane, 4 ml) was added dropwise to a stirred mixture of 3-(naphth-2-ylmethoxy)bromobenzene (1.88 g) and THF (30 ml) which had been cooled to −70° C. The mixture was stirred at −70° C. for 30 minutes. A solution of 1-ethoxycarbonylpyrrolidin-3-one (*J. Med. Pharm. Chem.*, 1962, 5, 755; 0.94 g) in THF (5 ml) was added, the mixture was allowed to warm to ambient temperature and stirred for 1 hour. Acetic acid (2 ml) and water (50 ml) were added in turn and the mixture was extracted with ethyl acetate. The organic phase was dried (Na$_2$SO$_4$) and evaporated. The residue was purified by column chromatography using increasingly polar mixtures of hexane and ethyl acetate as eluent. There was thus obtained 1-ethoxycarbonyl-3-hydroxy-3-[3-(naphth-2-ylmethoxy)phenyl]pyrrolidine (1.6 g, 68%) as a gum.

NMR Spectrum 1.26 (t, 3H), 2.1–2.4 (m, 2H), 3.6–3.9 (m, 4H), 4.15 (q, 2H), 5.23 (s, 2H), 6.96 (m, 1H), 7.04 (m, 1H), 7.18 (m, 1H), 7.30 (t, 1H), 7.46–7.56 (m, 3H), 7.81–7.89 (m, 4H).

Sodium hydride (50% dispersion in mineral oil, 0.17 g) was added portionwise to a stirred solution of a portion (1.2 g) of the 3-hydroxypyrrolidine so obtained in DMF (5 ml). The mixture was stirred at ambient temperature for 12 minutes. Methyl iodide (0.5 ml) was added and the mixture was stirred at ambient temperature for 1 hour. Acetic acid (2 ml) and water (50 ml) were added in turn and the mixture was extracted with ethyl acetate. The organic phase was dried (Na$_2$SO$_4$) and evaporated. The residue was purified by column chromatography using increasingly polar mixtures of hexane and ethyl acetate as eluent. There was thus obtained 1-ethoxycarbonyl-3-methoxy-3-[3-(naphth-2-ylmethoxy)phenyl]pyrrolidine (1.18 g, 95%) as a gum.

NMR Spectrum 1.27 (t, 3H), 2.17 (m, 1H), 2.4 (m, 1H), 2.99 (s, 3H), 3.57 (m, 3H}, 3.92 (m, 1H), 4.15 (q, 2H), 5.24 (s, 2H}, 6.97 (m, 2H), 7.06 (m, 1H), 7.29 (t, 1H), 7.46–7.56 (m, 3H), 7.82–7.89 (m, 4H).

EXAMPLE 2

Using an analogous procedure to that described in Example 1, 1-acetyl-3-methoxy-3-[3-(naphth-2-ylmethoxy)phenyl]pyrrolidine was reduced with lithium aluminium hydride to give 1-ethyl-3-methoxy-3-[3-naphth-2-ylmethoxy)phenyl]pyrrolidine in 65% yield as a solid, a portion of which was characterised as the hydrochloride salt, m.p. 88°–90° C. (recrystallised from ethyl acetate).

NMR Spectrum (CD$_3$OD+C$_5$D$_5$N) 1.37 (t, 3H), 2.52 (m, 1H), 2.65 (m, 1H), 3.0 (s, 3H), 3.3–3.45 (m, 3H), 3.55 (m, 1H), 3.7 (m, 1H), 3.95 (m, 1H), 5.31 (s, 2H), 7.02 (m, 1H), 7.36 (m, 1H), 7.48 (m, 2H), 7.56 (m, 1H), 7.85 (m, 4H).

The 1-acetyl-3-methoxy-3-[3-(naphth-2-ylmethoxy)phenyl]pyrrolidine used as a starting material was obtained as follows:

A mixture of 1-ethoxycarbonyl-3-methoxy-3-[3-(naphth-2-ylmethoxy)phenyl]pyrrolidine (0.3 g), aqueous sodium hydroxide (5N, 0.5 ml) and ethanol (2 ml) was stirred and heated to reflux for 48 hours. Water (10 ml) was added and the mixture was extracted with ethyl acetate. The organic phase was dried (Na$_2$SO$_4$) and evaporated. There was thus obtained 3-methoxy-3-[3-(naphth-2-ylmethoxy)phenyl]pyrrolidine (0.24 g, 97%) as a gum, a portion of which was characterised as the hydrochoride salt, m.p. 175°–176° C. (recrystallised from ethyl acetate).

A mixture of a portion (0.08 g) of the pyrrolidine so obtained and acetic anhydride (0.5 ml) was stirred and heated to 100° C. for 30 minutes. The mixture was evaporated and the residue was purified by column chromatography using increasingly polar mixtures of ethyl acetate and methanol as eluent. There was thus obtained 1-acetyl-3-methoxy-3-[3-(naphth-2-ylmethoxy)phenyl]pyrrolidine (0.07 g, 78%), m.p. 114°–116° C. (recrystallised from a mixture of methanol and water).

NMR Spectrum 2.06 (m, 3H), 2.1–2.6 (m, 3H), 2.99 (m, 3H), 3.5–4.1 (m, 4H), 5.24 (m, 2H), 6.9–7.1 (m, 3H), 7.25–7.4 (m, 1H), 7.45–7.6 (m, 3H), 7.9–7.95 (m, 4H).

EXAMPLE 3

A mixture of 3-methoxy-3-[3-(naphth-2-ylmethoxy)phenyl]pyrrolidine (0.2 g), 2,3-dichloroprop-1-ene (0.055 ml), potassium carbonate (0.2 g) and acetonitrile (3 ml) was stirred at ambient temperature for 18 hours. The mixture was partitioned between methylene chloride and water. The organic phase was dried (MgSO$_4$) and evaporated. The residue was purified by column chromatography using increasingly polar mixtures of methylene chloride and ethyl acetate as eluent. There was thus obtained 1-(2-chloroprop-2-enyl)-3-methoxy-3-[3-(naphth-2-ylmethoxy)phenyl]pyrrolidine (0.14 g, 57%) as an oil.

NMR Spectrum 2.15–2.4 (m, 2H), 2.85–3.1 (m, 7H), 3.37 (s, 2H), 5.24 (s, 2H), 5.32 (s, 2H), 5.43 (s, 2H), 6.93 (m, 1H), 7.02 (m, 1H), 7.11 (m, 1H), 7.27 (t, 1H), 7.45–7.57 (m, 3H), 7.85 (m, 4H).

EXAMPLE 4

Using an analogous procedure to that described in Example 3, 3-methoxy-3-[3-(naphth-2-ylmethoxy)phenyl]pyrrolidine was reacted with prop-2-ynyl bromide to give 3-methoxy-3-[3-(naphth-2-ylmethoxy)phenyl]-1-(prop-2-ynyl)pyrrolidine, m.p. 63°–65° C., in 11% yield.

NMR Spectrum 2.2–2.5 (m, 3H), 2.8–3.35 (m, 7H), 3.55 (d, 2H), 5.25 (s, 2H), 6.9–7.05 (m, 2H), 7.12 (m, 1H), 7.28 (t, 1H), 7.5 (m, 3H), 7.85 (m, 4H).

EXAMPLE 5

A mixture of 6-bromomethyl-1-ethyl-1,2-dihydroquinolin-2-one [European Patent Application No. 0385662, Example 7, Note c; 0.12 g], 3-(3-hydroxyphenyl)-3-methoxy-1-(2,2,2-trifluoroethyl)pyrrolidine (0.11 g), potassium carbonate (0.22 g) and DMF (3 ml) was stirred at ambient temperature for 1 hour. The mixture was partitioned between ethyl acetate and water. The organic phase was dried (Na$_2$SO$_4$) and evaporated. The residue was purified by column chromatography using increasingly polar mixtures of methylene chloride and ethyl acetate as eluent. There was thus obtained 3-[3-(1-ethyl-2-oxo-1,2-dihydroquinolin-6-ylmethoxy)phenyl]-3-methoxy-1-(2,2,2-trifluoroethyl)-pyrrolidine (0.12 g, 65%) as a gum.

NMR Spectrum 1.37 (t, 3H), 2.05–2.45 (m, 2H), 2.9–3.3 (m, 9H), 4.37 (q, 2H), 5.13 (s, 2H), 6.72 (d, 1H), 6.91 (m, 1H), 7.01 (m, 1H), 7.06 (m, 1H), 7.29 (t, 1H), 7.41 (m, 1H), 7.65 (m, 3H).

The 3-(3-hydroxyphenyl)-3-methoxy-1-(2,2,2-trifluoroethyl)pyrrolidine used as a starting material was obtained as follows:

Using an analogous procedure to that described in the portion of Example 1 which is concerned with the preparation of starting materials, 3-benzyloxybromobenzene was reacted with 1-ethoxycarbonylpyrroldin-3-one and the resultant product was reacted with methyl iodide. There was thus obtained 3-(3-benzyloxyphenyl)-1-ethoxycarbonyl-3-methoxypyrrolidine in 45% yield as a gum.

NNR Spectrum 1.27 (t, 3H), 2.13 (m, 1H), 2.4 (m, 1H), 3.0 (s, 3H), 3.53 (m, 3H), 3.9 (m, 1H), 4.16 (q, 2H), 5.07 (s, 2H), 6.92–7.0 (m, 3H), 7.24–7.42 (m, 6H).

Using an analogous procedure to that described in the portion of Example 2 which is concerned with the preparation of starting materials 3-(3-benzyloxyphenyl)-1-ethoxycarbonyl-3-methoxypyrrolidine was hydrolysed to give 3-(3-benzyloxyphenyl)-3-methoxypyrrolidine in 95% yield as an oil.

NMR Spectrum 2.0–2.45 (m, 2H), 3.0 (s, 3H), 3.1–3.5 (m, 4H), 5.07 (s, 2H), 6.8–7.0 (m, 3H), 7.2–7.5 (m, 6H).

A mixture of the pyrrolidine (1 g) so obtained, ethyl trifluoroacetate (3 ml), triethylamine (0.5 ml) and acetonitrile (10 ml) was stirred at ambient temperature for 2 hours. The mixture was evaporated and the residue was partitioned between ethyl acetate and water. The organic phase was dried (Na$_2$SO$_4$) and evaporated. The residue was purified by column chromatography using increasingly polar mixtures of hexane and ethyl acetate as eluent. There was thus obtained 3-(3-benzyloxyphenyl)-3-methoxy-1-(trifluoroacetyl)pyrrolidine (1 g, 75%) as a gum.

NMR Spectrum 2.1–2.4 (m, 1H), 2.4–2.6 (m, 1H), 3.0 (s, 3H), 3.65–3.95 (m, 3H), 4.15 (m, 1H), 5.09 (s, 2H), 6.9–7.05 (m, 3H), 7.25–7.5 (m, 6H).

Borane-THF complex (1M in THF, 1.6 ml) was added to a solution of a portion (0.3 g) of the pyrrolidine so obtained in THF (10 ml) and the mixture was stirred and heated to reflux for 1 hour. The mixture was cooled to ambient temperature and methanol (20 ml) was added. The mixture was evaporated and the residue was partitioned between a saturated aqueous sodium bicarbonate solution and methylene chloride. The organic phase was dried (MgSO$_4$) and evaporated to give 3-(3-benzyloxyphenyl)-3-methoxy-1-(2,2,2-trifluoroethyl)-pyrrolidine (0.27 g) as an oil which was used without further purification.

A mixture of the pyrrolidine so obtained, 10% palladium-on-charcoal catalyst (0.03 g) and glacial acetic acid (5 ml) was stirred under an atmospher of hydrogen for 30 minutes. The mixture was filtered and the filtrate was evaporated. There was thus obtained 3-(3-hydroxyphenyl)-3-methoxy-1-(2,2,2-trifluoroethyl)pyrrolidine (0.13 g, 65%) as a gum which was used without further purification.

EXAMPLE 6

A mixture of 6-mercapto-1-methyl-1,2,3,4-tetrahydroquinolin-2-one (0.125 g), 3-(3,5-difluorophenyl)-3-methoxy-1-(2,2,2-trifluoroethyl)pyrrolidine hydrochloride (0.2 g), lithium hydroxide monohydrate (0.06 g) and NMP (0.5 ml) was stirred and heated to 130° C. for 3 hours. The mixture was cooled to ambient temperature and partitioned between diethyl ether and water. The organic phase was dried (Na$_2$SO$_4$) and evaporated. The residue was purified by column chromatography using increasingly polar mixtures of methylene chloride and ethyl acetate as eluent. There was thus obtained 3-[5-fluoro-3-(1-methyl-2-oxo-1,2,3,4-tetrahydroquinolin-6-ylthio)phenyl]-3-methoxy-1-(2,2,2-trifluoroethyl)-pyrrolidine (0.11 g, 39%) as a gum.

NMR Spectrum 2.0–2.35 (m, 2H), 2.66 (m, 2H), 2.85–3.25 (m, 11H), 3.37 (s, 3H), 6.72 (m, 1H), 6.91 (m, 1H), 6.98 (d, 1H), 7.08 (m, 1H), 7.29 (m, 1H), 7.37 (m, 1H).

The 6-mercapto-1-methyl-1,2,3,4-tetrahydroquinolin-2-one used as a starting material was obtained as follows:

A mixture of concentrated hydrochloric acid (5 drops) and water (50 ml) was added to a stirred mixture of di-(1-methyl-2-oxo-1,2,3,4-tetrahydroquinolin-6-yl) disulphide (European Patent Application No. 0462812, Example 7 thereof; 38.4 g), triphenylphosphine (29 g) and 1,4-dioxan (300 ml). The mixture was stirred at ambient temperature for 30 minutes. The mixture was concentrated by evaporation to reduce the volume by approximately one half. The residue was partitioned between ethyl acetate and 0.5N aqueous sodium hydroxide solution. The aqueous phase was washed with diethyl ether and then acidified to pH2 by the addition of dilute aqueous hydrochloric acid. The acidic mixture was extracted with ethyl acetate. The organic phase was dried (MgSO$_4$) and evaporated. The residual oil was dissolved in diethyl ether and hexane was added. There was thus obtained 6-mercapto-1-methyl-1,2,3,4-tetrahydroquinolin-2-one as a solid (35.5 g, 92%) which was used without further purification.

The 3-(3,5-difluorophenyl)-3-methoxy-1-(2,2,2-trifluoroethyl)pyrrolidine hydrochloride used as a starting material was obtained as follows:

1-Benzylpyrrolidin-3-one (3.5 g) was added dropwise to a stirred, cooled (0° C.) solution of the Grignard reagent (0.6M in THF, 50 ml) obtained from 3,5-difluorobromobenzene and magnesium. The mixture was stirred at ambient temperature for 1 hour. The mixture was poured into water and extracted with diethyl ether. The organic phase was dried (Na$_2$SO$_4$) and evaporated. The residue was purified by column chromatography using increasingly polar mixtures of hexane and ethyl acetate as eluent. There was thus obtained 1-benzyl-3-(3,5-difluorophenyl)-3-hydroxypyrrolidine (3.1 g, 53%).

Sodium hydride (60% dispersion in mineral oil, 0.14 g) was added portionwise to a stirred solution of a portion (0.87 g) of the 3-hydroxypyrrolidine so obtained and 1,4,7,10,13-pentaoxacyclopentadecane (hereinafter 15-crown-5, 0.05 g) in DMF (10 ml). The mixture was stirred at ambient temperature for 15 minutes. A solution of methyl 4-toluenesulphonate (0–56 g) in THF (2 ml) was added dropwise and the mixture was stirred at ambient temperature for 2 hours. The mixture was partitioned between diethyl ether and water. The organic phase was dried (Na$_2$SO$_4$) and evaporated. The residue was purified by column chromatography using increasingly polar mixtures of hexane and ethyl acetate as eluent. There was thus obtained 1-benzyl-3-(3,5-difluorophenyl)-3-methoxypyrrolidine (0.82 g, 90%).

After appropriate repetition of the above-mentioned reaction, a mixture of 1-benzyl-3-(3,5-difluorophenyl)-3-methoxypyrrolidine (3.3 g), 10% palladium on charcoal catalyst (1 g), ammonium formate (0.75 g) and ethanol (30 ml) was stirred and heated to reflux for 1 hour. The mixture was filtered and evaporated. The residue was partitioned between ethyl acetate and 1N aqueous sodium hydroxide solution. The organic phase was washed with brine, dried ($Na_2SO_4$) and evaporated. There was thus obtained 3-(3,5-difluorophenyl)-3-methoxypyrrolidine as a gum (2.2 g, 95%).

A mixture of a portion (0.3 g) of the pyrrolidine so obtained, ethyl trifluoroacetate (0.5 ml), triethylamine (0.5 ml) and methanol (5 ml) was stirred at ambient temperature for 18 hours. The mixture was evaporated and the residue was partitioned between diethyl ether and 1N aqueous hydrochloric acid solution. The organic phase was washed with brine, dried ($Na_2SO_4$) and evaporated. There was thus obtained 3-(3,5-difluorophenyl)-3-methoxy-1-(trifluoroacetyl)pyrrolidine which was used without further purification.

Borane-THF complex (1M in THF, 3 ml) was added to a solution of the pyrrolidine so obtained in THF (3 ml) and the mixture was stirred and heated to reflux for 2 hours. The mixture was cooled to ambient temperature, methanol (10 ml) was added and the mixture was evaporated. The residue was dissolved in ethyl acetate (5 ml) and a saturated solution of hydrogen chloride in diethyl ether was added. Diethyl ether was added and the precipitate was collected. There was thus obtained 3-(3,5-difluorophenyl)-3-methoxy-1-(2,2,2-trifluoroethyl)pyrrolidine hydrochloride (0.35 g, 75%), m.p. 192°–194° C.

EXAMPLE 7

Using an analogous procedure to that described in Example 6, 6-mercapto-1-methyl-1,2,3,4-tetrahydroquinolin-2-one was reacted with 1-(2,2-difluoroethyl)-3-(3,5-difluorophenyl)-3-methoxypyrrolidine hydrochloride to give 3-[5-fluoro-3-(1-methyl-2-oxo-1,2,3,4-tetrahydroquinolin-6-ylthio)phenyl]-1-(2,2-difluoroethyl)-3-methoxypyrrolidine as a gum in 51% yield.

NMR Spectrum 2.0–2.35 (m, 2H), 2.68 (m, 2H), 2.8–3.1 (m, 11H), 3.37 (s, 3H), 5.85 (m, 1H), 6.72 (m, 1H), 6.92 (m, 1H), 7.0 (d, 1H), 7.1 (m, 1H), 7.31 (m, 1H), 7.39 (m, 1H).

The 1-(2,2-difluoroethyl)-3-(3,5-difluorophenyl)-3-methoxypyrrolidine hydrochloride used as a starting material was obtained as follows:

The procedures described in the last two paragraphs of the portion of Example 6 which is concerned with the preparation of starting materials were repeated except that ethyl difluoroacetate was used in place of ethyl trifluoroacetate. There was thus obtained the required starting material in 75% yield, m.p. 189°–191° C.

EXAMPLE 8

Using an analogous procedure to that described in Example 6, 6-mercapto-1-methyl-1,2,3,4-tetrahydroquinolin-2-one was reacted with 3-(3,5-difluorophenyl)-3-hydroxy-1-(2,2,2-trifluoroethyl)pyrrolidine to give 3-[5-fluoro-3-(1-methyl-2-oxo-1,2,3,4-tetrahydroquinolin-6-ylthio)phenyl]-3-hydroxy-1-(2,2,2-trifluoroethyl)pyrrolidine as a gum in 30% yield.

NMR Spectrum 2.05–2.4 (m, 2H), 2.6–2.7 (m, 3H), 2.8–3.1 (m, 5H), 3.1–3.35 (m, 3H), 3.37 (s, 3H), 6.7 (m, 1H), 6.98 (d, 1H), 7.02 (m, 1H), 7.21 (m, 1H), 7.28 (m, 1H), 7.36 (m, 1H).

The 3-(3,5-difluorophenyl)-3-hydroxy-1-(2,2,2-trifluoroethyl)pyrrolidine used as a starting material was obtained as follows:

Using 1-benzyl-3-(3,5-difluorophenyl)-3-hydroxypyrrolidine as the starting material rather than the corresponding 3-methoxypyrrolidine, the procedures described in the last three paragraphs of the portion of Example 6 which is concerned with the preparation of starting materials were repeated. There was thus obtained the required starting material as a gum in 70% yield.

EXAMPLE 9

Using an analogous procedure to that described in Example 6, 4-mercaptoacetanilide was reacted with 3-(3,5-difluorophenyl)-3-methoxy-1-(2,2,2-trifluoroethyl)pyrrolidine to give 3-[3-(4-acetamidophenylthio)-5-fluorophenyl]-3-methoxy-1-(2,2,2-trifluoroethyl)pyrrolidine in 54% yield, m.p. 127°–129° C.

NMR Spectrum 2.0–2.4 (m, 5H), 2.85–3.25 (m, 9H), 6.72 (m, 1H), 6.9 (m, 1H), 7.02 (m, 1H), 7.2 (broad s, 1H), 7.42 (m, 2H), 7.54 (m, 2H).

EXAMPLE 10

A mixture of 6-mercapto-1-methyl-1,2,3,4-tetrahydroquinolin-2-one (0.12 g), 3-(3-iodophenyl)-3-methoxy-1-(2,2,2-trifluoroethyl)pyrrolidine hydrochloride (0.21 g), cuprous(I) chloride (0.04 g), potassium carbonate (0.21 g) and DMF (3 ml) was stirred and heated to 120° C. for 2 hours. Second portions of the quinolin-2-one (0.06 g) and cuprous(I) chloride (0.02 g) were added and the mixture was heated to 120° C. for a further 2 hours. The mixture was cooled to ambient temperature and partitioned between diethyl ether and water. The organic phase was dried ($Na_2SO_4$) and evaporated. The residue was purified by column chromatography using increasingly polar mixtures of hexane and ethyl acetate as eluent. There was thus obtained 3-methoxy-3-[3-(1-methyl-2-oxo-1,2,3,4-tetrahydroquinolin-6-ylthio)phenyl]-1-(2,2,2-trifluoroethyl)pyrrolidine as a gum (0.095 g, 42%).

NMR Spectrum 2.0–2.4 (m, 2H), 2.66 (m, 2H), 2.85 (m, 2H), 2.95–3.3 (m, 9H), 3.36 (s, 3H), 6.95 (m, 1H), 7.15 (m, 1H), 7.2–7.45 (m, 5H).

The 3-(3-iodophenyl)-3-methoxy-1-(2,2,2-trifluoroethyl)pyrrolidine hydrochloride used as a starting material was obtained as follows:

Using analogous procedures to those described in the portion of Example 1 which is concerned with the preparation of starting materials, 1,3-diiodobenzene was converted into 1-ethoxycarbonyl-3-(3-iodophenyl)-3-methoxypyrrolidine as an oil in 38% yield.

A mixture of the material so obtained (2.65 g), 5N aqueous sodium hydroxide solution and ethanol (150 ml) was stirred and heated to reflux for 48 hours. The mixture was concentrated by the evaporation of most of the ethanol. The residue was partitioned between ethyl acetate and brine. The organic phase was dried ($Na_2SO_4$) and evaporated. There was thus obtained 3-(3-iodophenyl)-3-methoxypyrrolidine as an oil (1.7 g, 80%) which was used without further purification.

Using analogous procedures to those described in the last two paragraphs of the portion of Example 6 which is concerned with the preparation of starting materials, the product so obtained was converted into 3-(3-iodophenyl)-3-methoxy-1-(2,2,2-trifluoroethyl)pyrrolidine in 42% yield, m.p. 148°–150° C.

EXAMPLE 11

A mixture of 3-[5-fluoro-3-(1-methyl-2-oxo-1,2,3,4-tetrahydroquinolin-6-ylthio)phenyl]-3-hydroxy-1-(2,2,2-trifluoroethyl)pyrrolidine (0.062 g), sodium hydride (60% dispersion in mineral oil, 0.02 g), 15-crown-5 (0.01 g) and DMF (1 ml) was stirred at ambient temperature for 30 minutes. Ethyl bromide (0.011 ml) was added and the mixture was stirred at ambient temperature for 1 hour. The mixture was partitioned between diethyl ether and water. The organic phase was dried ($Na_2SO_4$) and evaporated. The residue was purified by column chromatography using increasingly polar mixtures of hexane and ethyl acetate as eluent. There was thus obtained 3-ethoxy-3-[5-fluoro-3-(1-methyl-2-oxo-1,2,3,4-tetrahydroquinolin-6-ylthio)phenyl]-1-(2,2,2-trifluoroethyl)pyrrolidine (0.11 g, 39%) as a gum.

NMR Spectrum 1.1 (t, 3H), 2.1 (m, 1H), 2.28 (m, 1H), 2.68 (m, 2H), 2.8–3.3 (m, 10H), 3.36 (s, 3H), 6.72 (m, 1H), 6.92 (m, 1H), 6.98 (d, 1H), 7.06 (m, 1H), 7.3 (m, 1H), 7.38 (m, 1H).

EXAMPLE 12

The procedure described in Example 11 was repeated except that 2-propynyl chloride was used in place of ethyl bromide. There was thus obtained 3-[5-fluoro-3-(1-methyl-2-oxo-1,2,3,4-tetrahydroquinolin-6-ylthio)phenyl]-3-(prop-2-ynyloxy)-1-(2,2,2-trifluoroethyl)pyrrolidine as a gum in 46% yield.

NMR Spectrum 2.15 (m, 1H), 2.2–2.5 (m, 2H), 2.68 (m, 2H), 2.9 (m, 2H), 2.95–3.35 (m, 6H), 3.36 (s, 3H), 3.85 (m, 2H), 6.74 (m, 1H), 6.94 (m, 1H), 7.0 (d, 1H), 7.08 (m, 1H), 7.4 (m, 1H), 7.48 (m, 1H).

EXAMPLE 13

The procedure described in Example 11 was repeated except that allyl chloride was used in place of ethyl bromide. There was thus obtained 3-allyloxy-3-[5-fluoro-3-(1-methyl-2-oxo-1,2,3,4-tetrahydroquinolin-6-ylthio)phenyl]-1-(2,2,2-trifluoroethyl)pyrrolidine as a gum in 46% yield.

NMR Spectrum 2.05–2.4 (m, 2H), 2.67 (m, 2H), 2.85–3.3 (m, 8H), 3.37 (s, 3H), 3.67 (m, 2H), 5.05–5.3 (m, 2H), 6.72 (m, 1H), 6.94 (m, 1H), 6.98 (d, 1H), 7.08 (m, 1H), 7.29 (m, 1H), 7.4 (m, 1H).

EXAMPLE 14

A mixture of 3-[5-fluoro-3-(1-methyl-2-oxo-1,2,3,4-tetrahydroquinolin-6-ylthio)phenyl]-3-methoxy-1-(2,2,2-trifluoroethyl)pyrrolidine (0.075 g), potassium peroxymonosulphate (0.12 g), sulphuric acid (20%, 0.5 ml) and ethanol (2 ml) was stirred at ambient temperature for 18 hours. Crushed ice (10 ml) was added and the mixture was basified by the addition of a concentrated aqueous ammonium hydroxide solution. The mixture was extracted with ethyl acetate. The organic phase was dried ($Na_2SO_4$) and evaporated. The residue was purified by column chromatography using increasingly polar mixtures of hexane and ethyl acetate as eluent. There was thus obtained 3-[5-fluoro-3-(1-methyl-2-oxo-1,2,3,4-tetrahydroquinolin-6-ylsulphonyl)phenyl]-3-methoxy-1-(2,2,2-trifluoroethyl)pyrrolidine as a gum (0.058 g, 72%).

NMR Spectrum 2.12 (m, 1H), 2.32 (m, 1H), 2.68 (m, 2H), 2.9–3.25 (m, 1H), 3.36 (s, 3H), 7.08 (d, 1H), 7.35 (m, 1H), 7.53 (m, 1H), 7.74 (m, 1H), 7.8–7.9 (m, 2H).

EXAMPLE 15

Using an analogous procedure to that described in Example 14, 3-methoxy-3-[3-(1-methyl-2-oxo-1,2,3,4-tetrahydroquinolin-6-ylthio)phenyl]-1-(2,2,2-trifluoroethyl)pyrrolidine was oxidised to give 3-methoxy-3-[3-(1-methyl-2-oxo-1,2,3,4-tetrahydroquinolin-6-ylsulphonyl)phenyl]-1-(2,2,2-trifluoroethyl)pyrrolidine as a gum in 53% yield.

NMR Spectrum 2.15 (m, 1H), 2.35 (m, 1H), 2.68 (m, 2H), 2.9–3.28 (m, 1H), 3.35 (s, 3H), 7.06 (d, 1H), 7.5 (m, 1H), 7.63 (m, 1H), 7.73 (m, 1H), 7.8–7.9 (m, 2H), 7.99 (m, 1H).

EXAMPLE 16

3-Chloroperoxybenzoic acid (50% strength, 0.017 g) was added to a stirred solution of 3-[5-fluoro-3-(1-methyl-2-oxo-1,2,3,4-tetrahydroquinolin-6-ylthio)phenyl]-3-methoxy-1-(2,2,2-trifluoroethyl)pyrrolidine (0.027 g) in methylene chloride (5 ml) which had been cooled to 0° C. The mixture was stirred at a temperature in the range 0° to 5° C. for 1 hour. The mixture was partitioned between ethyl acetate and 1N aqueous sodium hydroxide solution. The organic phase was dried ($Na_2SO_4$) and evaporated. The residue was purified by column chromatography using increasingly polar mixtures of methylene chloride and ethyl acetate as eluent. There was thus obtained 3-[5-fluoro-3-(1-methyl-2-oxo-1,2,3,4-tetrahydroquinolin-6-ylsulphinylphenyl]-3-methoxy-1-(2,2,2-trifluoroethyl)pyrrolidine (0.01 g, 40%) as a gum.

NMR Spectrum 2.0–2.4 (m, 2H), 2.65 (m, 2H), 2.85–3.25 (m, 11H), 3.36 (s, 3H), 7.05 (d, 1H), 7.15–7.35 (m, 2H), 7.38–7.42 (m, 3H).

EXAMPLE 17

Using an analogous procedure to that described in Example 3 except that diisopropylethylamine was used in place of potassium carbonate, 3-methoxy-3-[3-(1-methyl-2-oxo-1,2-dihydroquinolin-6-ylmethoxy)phenyl]pyrrolidine was reacted with 2-propynyl bromide to give 3-methoxy-3-[3-(1-methyl-2-oxo-1,2-dihydroquinolin-6-ylmethoxy)phenyl]-1-(prop-2-ynyl)pyrrolidine as a gum in 21% yield.

NMR Spectrum 2.1–2.45 (m, 3H), 2.85–3.25 (m, 7H), 3.52 (m, 2H), 3.73 (s, 3H), 5.14 (s, 2H), 6.72 (d, 1H), 6.9 (m, 1H), 6.96–7.1 (m, 2H), 7.22–7.45 (m, 2H), 7.6–7.8 (m, 3H).

The 3-methoxy-3-[3-(1-methyl-2-oxo-1,2-dihydroquinolin-6-ylmethoxy)phenyl]pyrrolidine used as a starting material was obtained as follows:

A mixture of 3-(3-benzyloxyphenyl)-3-methoxy-1-(trifluoroacetyl)pyrrolidine (0.6 g), 10% palladium on charcoal catalyst (0.1 g) and glacial acetic acid (5 ml) was stirred under an atmosphere of hydrogen gas for 1 hour. The mixture was filtered and evaporated. There was thus obtained 3-(3-hydroxyphenyl)-3-methoxy-1-(trifluoroacetyl)pyrrolidine as a gum (0.43 g, 93%).

Using an analogous procedure to that described in Example 5, 3-(3-hydroxyphenyl)-3-methoxy-1-(trifluoroacetyl)pyrrolidine was reacted with 6-bromomethyl-1-methyl-1,2-dihydroquinolin-2-one [European Patent Application No. 0385662, Example 6 thereof] to give 3-methoxy-3-[3-(1-methyl-2-oxo-1,2-dihydroquinolin-6-ylmethoxy)phenyl]-1-(trifluoroacetyl)pyrrolidine as a gum in 70% yield.

A mixture of the product so obtained (1 g), potassium carbonate (0.5 g), methanol (5 ml) and water (5 ml) was stirred at ambient temperature for 2 hours. The mixture was evaporated and the residue was purified using a 9:1:0.1 mixture of methylene chloride, methanol and concentrated ammonium hydroxide solution as eluent. There was thus obtained the required starting material as a gum (0.66 g, 83%).

EXAMPLE 18

The procedure described in Example 17 was repeated except that 2-iodoacetamide was used in place of 2-propynyl bromide. There was thus obtained 1-(carbamoylmethyl)-3-methoxy-3-[3-(1-methyl-2-oxo-1,2-dihydroquinolin-6-ylmethoxy)phenyl]pyrrolidine as a gum in 44% yield.

NMR Spectrum 2.15–2.45 (m, 2H), 2.8–3.2 (m, 7H), 3.26 (s, 2H), 3.73 (s, 3H), 5.13 (s, 2H), 5.45 (broad s, 1H), 6.73 (d, 1H), 6.85–7.1 (m, 4H), 7.3 (t, 1H), 7.39 (d, 1H), 7.6–7.75 (m, 3H).

EXAMPLE 19

A mixture of 3-methoxy-3-[3-(1-methyl-2-oxo-1,2-dihydroquinolin-6-ylmethoxy)phenyl]pyrrolidine (0.11 g), acrylonitrile (0.5 ml) and acetonitrile (2 ml) was stirred and heated to reflux for 10 hours. The mixture was evaporated and the residue was purified by column chromatography using increasingly polar mixtures of methylene chloride and methanol as eluent. There was thus obtained 1-(2-cyanoethyl)-3-methoxy-3-[3-(1-methyl-2-oxo-1,2-dihydroquinolin-6-ylmethoxy)phenyl]pyrrolidine as a gum (0.051 g, 41%).

NMR Spectrum 2.15–2.45 (m, 3H), 2.56 (t, 2H), 2.78–3.12 (m, 9H), 3.73 (s, 3H), 5.14 (s, 2H), 6.72 (d, 1H), 6.9 (m, 1H), 6.95–7.1 (m, 2H), 7.22–7.45 (m, 2H), 7.6–7.75 (m, 3H).

EXAMPLE 20

Using an analogous procedure to that described in Example 3, 3-methoxy-3-[3-(naphth-2-ylmethoxy)phenyl]pyrrolidine was reacted with 2-chloroacetonitrile to give 1-(cyanomethyl)-3-methoxy-3-[3-(naphth-2-ylmethoxy)phenyl]pyrrolidine in 45% yield, m.p. 76°–77° C. (recrystallised from methanol).

NMR Spectrum 2.2–2.5 (m, 2H), 2.8–3.2 (m, 7H), 3.7 (s, 2H), 5.24 (s, 2H), 6.9–7.02 (m, 2H), 7.07 (m, 1H), 7.29 (t, 1H), 7.45–7.58 (m, 3H), 7.8–7.95 (m, 4H).

EXAMPLE 21

Using an analogous procedure to that described in Example 3, 3-methoxy-3-[3-(naphth-2-ylmethoxy)phenyl]pyrrolidine was reacted with methyl bromoacetate to give 3-methoxy-1-(methoxycarbonylmethyl)-3-[3-(naphth-2-ylmethoxy)phenyl]pyrrolidine in 33Z yield, m.p. 78°–80° C.

NMR Spectrum 2.15–2.4 (m, 2H), 2.9–3.05 (m, 5H), 3.14 (s, 2H), 3.46 (s, 2H), 3.73 (s, 3H), 5.24 (s, 2H), 6.93 (m, 1H), 7.02 (m, 1H), 7.11 (m, 1H), 7.27 (t, 1H), 7.45–7.6 (m, 3H), 7.8–7.92 (m, 4H).

EXAMPLE 22

Borane-THF complex (1M in THF, 0.56 ml) was added to a solution of 1-(difluoroacetyl)-3-methoxy-3-[3-(naphth-2-ylmethoxy)phenyl]pyrrolidine (0.076 g) in THF (2 ml). The mixture was stirred and heated to reflux for 1.5 hours. Methanol (10 ml) was added and the mixture was evaporated. The residue was partitioned between ethyl acetate and water. The organic phase was dried (Na$_2$SO$_4$) and evaporated. The residue was purified by column chromatography using increasingly polar mixtures of hexane and ethyl acetate as eluent. There was thus obtained 1-(2,2-difluoroethyl)-3-methoxy-3-[3-(naphth-2ylmethoxy)phenyl]pyrrolidine as a gum (0.031 g, 42%).

NMR Spectrum 2.4 (m, 1H), 2.65 (m, 1H), 2.98 (s, 3H), 3.2–3.65 (m, 6H), 5.33 (s, 2H), 6.6 (m, 1H), 6.9–7.05 (m, 3H), 7.3 (m, 1H), 7.45–7.6 (m, 3H), 7.8–7.95 (m, 4H).

The 1-(difluoroacetyl)-3-methoxy-3-[3-(naphth-2-ylmethoxy)phenyl]pyrrolidine used as a starting material was obtained as follows:

Using an analogous procedure to that described in the third paragraph of the portion of Example 5 which is concerned with the preparation of starting materials, 3-methoxy-3-[3-(naphth-2-ylmethoxy)phenyl]pyrrolidine was reacted with ethyl difluoroacetate. There was thus obtained the required starting material as a gum in 68% yield.

EXAMPLE 23

Sodium hydride (50% dispersion in oil, 0.036 g) was added to a stirred mixture of 3-[3-{4-acetamidophenylthio)-5-fluorophenyl]-3-methoxy-1-(2,2,2-trifluoroethyl)pyrrolidine (0.22 g), 15-crown-5 (0.02 g) and DMF (3 ml). The mixture was stirred at ambient temperature for 30 minutes. Methyl 4-toluenesulphonate (0.1 ml) was added and the mixture was stirred at ambient temperature for 1 hour. The mixture was partitioned between diethyl ether and water. The organic phase was dried (Na$_2$SO$_4$) and evaporated. The residue was purified by column chromatography using increasingly polar mixtures of hexane and ethyl acetate as eluent. There was thus obtained 3-{5-fluoro-3-[4-(N-methylacetamido)phenylthio]phenyl}-3-methoxy-1-(2,2,2-trifluoroethyl)pyrrolidine as a gum (0.15 g, 68%).

NMR Spectrum 1.92 (s, 3H), 2.14 (m, 1H), 2.3 (m, 1H), 2.9–3.25 (m, 9H), 3.28 (s, 3H), 6.9 (m, 1H), 7.02 (m, 1H), 7.1–7.2 (m, 3H), 7.4 (m, 2H).

EXAMPLE 24

Using an analogous procedure to that described in Example 10, 4'-mercaptoacetophenone was reacted with 3-(3-iodophenyl)-3-methoxy-1-(2,2,2-trifluoroethyl)pyrrolidine hydrochloride to give 3-[3-(4-acetylphenylthio)phenyl]-3-methoxy-1-(2,2,2-trifluoroethyl)pyrrolidine as a gum in 75% yield.

NMR Spectrum 2.1–2.4 (m, 2H), 2.56 (s, 3H), 2.95–3.3 (m, 9H), 7.22 (m, 2H), 7.4 (m, 3H), 7.53 (m, 1H), 7.82 (m, 2H).

The 4'-mercaptoacetophenone used as a starting material was obtained as follows:

A mixture of sodium hydrosulphide hydrate (NaSH, 33.6 g) and N-methylmorpholine (220 ml) was stirred and heated to 160° C. The mixture was partially evaporated under vacuum to remove the water. A solution of 4'-bromoacetophenone (40 g) in NMP (30 ml) was added dropwise to the residue and the mixture was stirred and heated to 160° C. for 90 minutes. The mixture was evaporated and the residue was poured into a mixture of ethyl acetate, water and ice. The aqueous phase was acidified to pH2 by the addition of dilute aqueous hydrochloric acid and extracted with ethyl acetate. The organic extract was washed with brine, dried (MgSO$_4$) and evaporated. There was thus obtained 4'-mercaptoacetophenone as an oil (25 g) which was used without further purification.

EXAMPLE 25

Using an analogous procedure to that described in Example 3 except that diisopropylethylamine was used in place of potassium carbonate, 3-[3-(4-acetylphenyl-thio)phenyl]-3-methoxypyrrolidine was reacted with 2-propynyl bromide to give 3-[3-(4-acetylphenylthio)-phenyl]-3-methoxy-1-(prop-2-ynyl)pyrrolidine as a gum in 14% yield.

NMR Spectrum 2.1–2.4 (m, 3H), 2.56 (m, 3H), 2.8–3.3 (m, 7H), 3.5 (m, 2H), 7.22 (m, 2H), 7.37–7.5 (m, 3H), 7.56 (m, 1H), 7.82 (m, 2H).

The 3-[3-(4-acetylphenylthio)phenyl]-3-methoxypyrrolidine used as a starting material was obtained as follows:

Using an analogous procedure to that described in Example 10, 4'-mercaptoacetophenone was reacted with 1-ethoxycarbonyl-3-(3-iodophenyl)-3-methoxypyrrolidine to give 3-[3-(4-acetylphenylthio)phenyl]-1-ethoxycarbonyl-3-methoxypyrrolidine as a gum in 24% yield.

A mixture of the product so obtained (0.4 g), trimethylsilyl iodide (0.4 g), diisopropylethylamine (0.52 g) and chloroform (5 ml) was stirred and heated to reflux for 4 hours. The mixture was cooled to ambient temperature. Water (10 ml) and diethyl ether (30 ml) were added and the mixture was stirred at ambient temperature for 12 minutes. The organic phase was separated. The aqueous phase was extracted with diethyl ether. The organic phases were combined, dried ($Na_2SO_4$) and evaporated. There was thus obtained 3-[3-(4-acetylphenylthio)-phenyl]-3-methoxypyrrolidine as a gum (0.3 g, 91%) which was used without further purification.

EXAMPLE 26

A mixture of 4'-fluoroacetophenone (0.1 g), 3-(2-mercaptothien-4-yl)-3-methoxy-1-(2,2,2-trifluoroethyl)pyrrolidine (0.27 g), potassium carbonate (0.26 g) and DMF (4 ml) was stirred and heated to 140° C. for 1 hour. The mixture was cooled to ambient temperature and partitioned between ethyl acetate and water. The organic phase was dried ($Na_2SO_4$) and evaporated. The residue was purified by column chromatography using increasingly polar mixtures of hexane and ethyl acetate as eluent. There was thus obtained 3-[2-(4-acetylphenylthio)thien-4-yl]-3-methoxy-1-(2,2,2-trifluoroethylpyrrolidine as an oil (0.153 g, 50%).

NMR Spectrum 2.2 (m, 1H), 2.35 (m, 1H), 2.55 (s, 3H), 2.9–3.3 (m, 9H), 7.18 (m, 2H), 7.30 (m, 1H), 7.38 (m, 1H), 7.83 (m, 2H).

The 3-(2-mercaptothien-4-yl)-3-methoxy-1-(2,2,2-trifluoroethyl)pyrrolidine used as a starting material was obtained as follows:

n-Butyl-lithium (1.6M in THF, 28.5 ml) was added to a stirred mixture of 2,4-dibromothiophene (*J. Org. Chem.*, 1988, 53, 417; 10 g) and diethyl ether (150 ml) which had been cooled to −70° C. After 1 hour, a solution of dimethyl disulphide (3 ml) in diethyl ether (10 ml) was added and the mixture was stirred and allowed to warm to −20° C. during 1 hour. The mixture was poured into water. The organic phase was washed with brine, dried ($MgSO_4$) and evaporated. The residue was purified by column chromatography using hexane as eluent. There was thus obtained 4-bromo-2-methylthiothiophene (4.76 g, 90%).

n-Butyl-lithium (1.5M in hexane, 6.7 ml) was added dropwise to a stirred mixture of 4-bromo-2-methylthiothiophene (2.09 g) in diethyl ether (30 ml) which had been cooled to −70° C. The mixture was stirred at −70° C. for 6 minutes. A solution of 1-ethoxycarbonyl-pyrrolidin-3-one (1.57 g) in diethyl ether (5 ml) was added. The mixture was stirred for 1 hour and allowed to warm to ambient temperature. A saturated aqueous ammonium chloride solution (100 ml) was added and the mixture was extracted with ethyl acetate. The organic extract was dried ($Na_2SO_4$) and evaporated. The residue was purified by column chromatography using increasingly polar mixtures of methylene chloride and ethyl acetate as eluent. There was thus obtained 1-ethoxycarbonyl-3-hydroxy-3-(2-methylthiothien-4-yl)pyrrolidine as a gum (1.7 g, 60%).

Using an analogous procedure to that described in the second paragraph of the portion of Example 1 which is concerned with the preparation of starting materials, 1-ethoxycarbonyl-3-hydroxy-3-(2-methylthiothien-4-yl)pyrrolidine was reacted with methyl iodide to give 1-ethoxycarbonyl-3-methoxy-3-(2-methylthiothien-4-yl)pyrrolidine as an oil in 75% yield.

Using an analogous procedure to that described in the first paragraph of the portion of Example 2 which is concerned with the preparation of starting materials, the 1-ethoxycarbonylpyrrolidine so obtained was hydrolysed to give 3-methoxy-3-(2-methylthiothien-4-yl)pyrrolidine as an oil in 73% yield.

Using analogous procedures to those described in the third and fourth paragraphs of the portion of Example 5 which is concerned with the preparation of starting materials, the pyrrolidine so obtained was converted into 3-methoxy-3-(2-methylthiothien-4-yl)-1-(2,2,2-trifluoroethyl)pyrrolidine as an oil in 63% yield.

A mixture of the product so obtained (0.23 g), sodium methanethiolate (0.08 g) and DMF (3 ml) was stirred and heated to 130° C. for 2.5 hours. The mixture was cooled to ambient temperature and partitioned between diethyl ether and water. The aqueous phase was acidified to pH4 by the addition of 1M aqueous citric acid and extracted with diethyl ether. The resultant extract was dried ($Na_2SO_4$) and evaporated. There was thus obtained 3-(2-mercaptothien-4-yl)-3-methoxy-1-(2,2,2-trifluoroethyl)pyrrolidine as an oil (0.2 g, 98%).

EXAMPLE 27

A mixture of 3-[2-(4-acetylphenylthio)thien-4-yl]-3-methoxy-1-(2,2,2-trifluoroethyl)pyrrolidine (0.13 g), hydroxylamine hydrochloride (0.06 g), sodium acetate (0.15 g) and ethanol (3 ml) was stirred and heated to reflux for 1.5 hours. The mixture was allowed to cool to ambient temperature. Water (10 ml) was added and the mixture was extracted with ethyl acetate. The organic phase was dried ($Na_2SO_4$) and evaporated. The residue was purified by column chromatography using increasingly polar mixtures of methylene chloride and ethyl acetate as eluent. There was thus obtained 3-{2-[4-(1-hydroxyiminoethyl)phenylthio]thien-4-yl}-3-methoxy-1-(2,2,2-trifluoroethyl)pyrrolidine as a gum (0.08 g, 60%).

NMR Spectrum 2.1–2.4 (m, 5H), 2.9–3.3 (m, 9H), 7.18 (m, 2H), 7.25 (m, 1H), 7.31 (m, 1H), 7.42 (s, 1H), 7.53 (m, 2H).

EXAMPLE 28

Using an analogous procedure to that described in Example 27, 3-[2-(4-acetylphenylthio)thien-5-yl]-3-methoxy-1-(2,2,2-trifluoroethyl)pyrrolidine was reacted with hydroxylamine hydrochloride to give 3-{2-[4-(1-hydroxyiminoethyl)phenylthio]thien-5-yl}-3-methoxy-1-(2,2,2-trifluoroethyl)pyrrolidine as a gum in 63% yield.

NMR Spectrum 2.1–2.4 (m, 5H), 2.95–3.3 (m, 9H), 6.94 (m, 1H), 7.15–7.21 (m, 3H), 7.44 (s, 1H), 7.53 (m, 2H).

The 3-[2-(4-acetylphenylthio)thien-5-yl]-3-methoxy-1-(2,2,2-trifluoroethyl)pyrrolidine used as a starting material was obtained as follows:

A solution of 4′-mercaptoacetophenone (25 g) in DMSO (100 ml) was stirred at ambient temperature for 16 hours. The mixture was poured onto a mixture of ice and water and extracted with ethyl acetate. The organic extract was washed with brine, dried (MgSO₄) and evaporated. The residue was purified by column chromatography using a 7:3 mixture of petroleum ether (b.p. 40°–60° C.) and ethyl acetate as eluent. There was thus obtained di-(4-acetylphenyl) disulphide (16.3 g, 65%), m.p. 94°–95° C.

A mixture of di-(4-acetylphenyl) disulphide (1.9 g), ethylene glycol (2.45 ml), triethyl orthoformate (5 ml), 4-toluenesulphonic acid (0.041 g) and toluene (22 ml) was stirred and heated to 45° C. for 2 hours. The mixture was cooled to ambient temperature, washed with a saturated aqueous sodium bicarbonate solution, dried (MgSO₄) and evaporated. The residue was purified by column chromatography using a 3:7 mixture of petroleum ether (b.p. 40°–60° C.) and ethyl acetate as eluent. There was thus obtained di-[4-(2-methyl-1,3-dioxolan-2-yl)phenyl]disulphide (2.12 g, 99%), m.p. 135°–137° C.

n-Butyl-lithium (1.6M in hexane, 4.23 ml) was added dropwise to a stirred solution of 2,4-dibromothiophene (1.74 g) in diethyl ether (60 ml) which had been cooled to −70° C. The mixture was stirred at −70° C. for 30 minutes. A solution of di-[4-(2-methyl-1,3-dioxolan-2-yl)phenyl]disulphide (2.29 g) in THF (25 ml) was added. The mixture was stirred at −70° C. for 30 minutes and then allowed to warm to ambient temperature. The mixture was poured into a saturated aqueous ammonium chloride solution and extracted with diethyl ether. The organic phase was washed with a dilute aqueous potassium carbonate solution, with water and with brine, dried (MgSO₄) and evaporated. The residue was purified by column chromatography using a 10:1 mixture of hexane and ethyl acetate as eluent. There was thus obtained 4′-(4-bromothien-2-ylthio)acetophenone ethylene acetal (1.64 g, 78%) as an oil;

NMR Spectrum 1.65 (s, 3H), 3.7–3.8 (m, 2H), 4.0–4.1 (m, 2H), 7.2–7.5 (m, 6H).

After appropriate repetition of the last-mentioned step, n-butyl-lithium (1.5M in hexane, 4.2 ml) was added dropwise to a stirred solution of 4′-(4-bromothien-2-ylthio)acetophenone ethylene acetal (2.09 g) in THF (50 ml) which had been cooled to −70° C. The mixture was stirred at −70° C. for 12 minutes. A solution of 1-ethoxycarbonylpyrrolidin-3-one (1.57 g) in THF (5 ml) was added. The mixture was stirred for 1 hour and allowed to warm to ambient temperature. A saturated aqueous ammonium chloride solution (100 ml) was added and the mixture was extracted with ethyl acetate. The organic phase was dried (Na₂SO₄) and evaporated. The residue was purified by column chromatography using increasingly polar mixtures of methylene chloride and ethyl acetate as eluent. There was thus obtained 1-ethoxycarbonyl-3-hydroxy-3-{2-[4-(2-methyl-1,3-dioxolan-2-yl)phenylthio]thien-5-yl}pyrrolidine as a gum (0.85 g, 60%).

Using an analogous procedure to that described in the second paragraph of the portion of Example 1 which is concerned with the preparation of starting materials, the pyrrolidine so obtained was reacted with methyl iodide to give 1-ethoxycarbonyl-3-methoxy-3-{2-[4-(2-methyl-1,3-dioxolan-2-yl)phenylthio]thien-5-yl}pyrrolidine as a gum in 73% yield.

Using an analogous procedure to that described in the first paragraph of the portion of Example 2 which is concerned with the preparation of starting materials, the pyrrolidine so obtained was hydrolysed to give 3-methoxy-3-{2-[4-(2-methyl-1,3-dioxolan-2-yl)phenylthio]thien-5-yl}pyrrolidine as a gum in 79% yield.

Using an analogous procedure to that described in the third paragraph of the portion of Example 5 which is concerned with the preparation of starting materials, the pyrrolidine so obtained was reacted with ethyl trifluoroacetate to give 3-methoxy-3-{2-[4-(2-methyl-1,3-dioxolan-2-yl)phenylthio]thien-5-yl}-1-(trifluoroacetyl)pyrrolidine as a gum in 60% yield.

Borane-THF complex (1.5M in THF, 0.45 ml) was added to a solution of the pyrrolidine so obtained (0.14 g) in THF (2 ml). The mixture was stirred and heated to reflux for 1 hour. Methanol (10 ml) was added and the mixture was evaporated. A mixture of the resultant residue, 2N aqueous hydrochloric acid (0.5 ml) and acetone (2 ml) was stirred at ambient temperature for 18 hours. The mixture was basified by the addition of a saturated aqueous sodium bicarbonate solution and extracted with ethyl acetate. The organic phase was dried (Na₂SO₄) and evaporated. The residue was purified by column chromatography using increasingly polar mixtures of hexane and ethyl acetate as eluent. There was thus obtained 3-[2-(4-acetylphenylthio)thien-5-yl]-3-methoxy-1-(2,2,2-trifluoroethyl)pyrrolidine as a gum in 54% yield.

EXAMPLE 29

Using an analogous procedure to that described in Example 27, 3-[3-(4-acetylphenylthio)phenyl]-3-methoxy-1-(2,2,2-trifluoroethyl)pyrrolidine was reacted with hydroxylamine hydrochloride to give 3-{3-[4-(1-hydroxyiminoethyl)phenylthio]phenyl}-3-methoxy-1-(2,2,2-trifluoroethyl)pyrrolidine in 63% yield, m.p. 86°–88° C.

NMR Spectrum 2.1–2.4 (m, 5H), 2.95–3.3 (m, 9H), 7.2–7.35 (m, 5H), 7.42 (m, 1H), 7.57 (m, 2H), 8.55 (broad s, 1H).

EXAMPLE 30

Sodium hydride (60% dispersion in mineral oil, 0.016 g) was added portionwise to a stirred mixture of 3-{3-[4-(1-hydroxyiminoethyl)phenylthio]phenyl}-3-methoxy-1-(2,2,2-trifluoroethyl)pyrrolidine (0.12 g), bromoacetonitrile (0.05 g) and DMF (2 ml) which had been cooled to 0° C. The mixture was stirred at 0° C. for 1 hour. Acetic acid (0.1 ml) and water (10 ml) were added and the mixture was extracted with diethyl ether. The organic phase was dried (Na₂SO₄) and evaporated. The residue was purified by column chromatography using increasingly polar mixtures of methylene chloride and ethyl acetate as eluent. There was thus obtained 3-{3-[4-(1-cyanomethoxyiminoethyl)phenylthio]phenyl}-3-methoxy-1-(2,2,2-trifluoroethyl)pyrrolidine as a gum (0.065 g, 70%).

NMR Spectrum 2.1–2.4 (m, 5H), 2.95–3.3 (m, 9H), 4.81 (s, 2H), 7.2–7.35 (m, 5H), 7.45 (m, 1H), 7.58 (m, 2H).

EXAMPLE 31

Using an analogous procedure to that described in Example 27, 3-[3-(4-acetylphenylthio)-5-fluorophenyl]-

3-methoxy-1-(prop-2-ynyl)pyrrolidine was reacted with hydroxylamine hydrochloride to give 3-{5-fluoro-3-[4-(1-hydroxyiminoethyl)phenylthio]phenyl}-3-methoxy-1-(prop-2-ynyl)pyrrolidine in 96% yield, m.p. 97°–99° C. (recrystallised from a mixture of hexane and diethyl ether).

NMR Spectrum 2.1–2.4 (m, 6H), 2.8–3.15 (m, 7H), 3.5 (m, 2H), 6.85 (m, 1H), 7.02 (m, 1H), 7.3 (m, 1H), 7.38 (m, 2H), 7.62 (m, 2H), 7.8 (broad s, 1H).

The 3-[3-(4-acetylphenylthio)-5-fluorophenyl]-3-methoxy-1-(prop-2-ynyl)pyrrolidine used as a starting material was obtained as follows:

A mixture of di-[4-(2-methyl-1,3-dioxolan-2-yl)phenyl]disulphide (2 g), triphenylphosphine (1.41 g), water (3 ml) and 1,4-dioxan (20 ml) was stirred and heated to 70° C. for 7 hours. The mixture was evaporated and the residue was partitioned between diethyl ether and 1N aqueous sodium hydroxide solution. The aqueous phase was acidified to pH6 by the addition of 6N aqueous hydrochloric acid and extracted with diethyl ether. The organic extract was washed with brine, dried (MgSO$_4$) and evaporated. There was thus obtained 4-(2-methyl-1,3-dioxolan-2-yl)benzenethiol (1.4 g, 70%) as an oil.

After appropriate repetition of the above-mentioned step a mixture of the thiol so obtained (9.8 g), 1-bromo-3,5-difluorobenzene (11.6 g), lithium hydroxide hydrate (2.52 g) and NMP (30 ml) was stirred and heated to 75° C. for 18 hours. The mixture was cooled to ambient temperature and partitioned between diethyl ether and water. The organic phase was washed with brine, dried (MgSO$_4$) and evaporated. The residue was purified by column chromatography using increasingly polar mixtures of hexane and ethyl acetate as eluent. There was thus obtained 5-fluoro-3-[4-(2-methyl-1,3-dioxolan-2-yl)phenylthio]bromobenzene (13.36 g, 72%}, m.p. 62°–64° C.

Using an analogous procedure to that described in the fourth paragraph of the portion of Example 28 which is concerned with the preparation of starting materials, 5-fluoro-3-[4-(2-methyl-1,3-dioxolan-2-yl)phenylthio]bromobenzene was reacted with 1-ethoxycarbonylpyrrolidin-3-one to give 1-ethoxycarbonyl-3-{5-fluoro-3-[4-(2-methyl1,3-dioxolan-2-yl)phenylthio]phenyl}-3-hydroxypyrrolidine as a gum in 50% yield.

Using an analogous procedure to that described in the second paragraph of the portion of Example 1 which is concerned with the preparation of starting materials, the pyrrolidine so obtained was reacted with methyl iodide to give 1-ethoxycarbonyl-3-{5-fluoro-3-[4-(2-methyl-1,3-dioxolan-2-yl)phenylthio]phenyl}-3-methoxypyrrolidine as a gum in 82% yield.

Using an analogous procedure to that described in the first paragraph of the portion of Example 2 which is concerned with the preparation of starting materials, the pyrrolidine so obtained was hydrolysed to give 3-{5-fluoro-3-[4-(2-methyl-1,3-dioxolan-2-yl)phenylthio]phenyl}-3-methoxypyrrolidine as a gum in 82% yield.

Using an analogous procedure to that described in Example 3 except that diisopropylethylamine was used in place of potassium carbonate, the pyrrolidine so obtained was reacted with 2-propynyl bromide to give 3-{5-fluoro-3-[4-(2-methyl-1,3-dioxolan-2-yl)phenylthio]phenyl}-3-methoxy-1-(prop-2-ynyl)pyrrolidine as a gum in 55% yield.

A mixture of the pyrrolidine so obtained (0.055 g), 2N aqueous hydrochloric acid (0.1 ml) and acetone (20 ml) was stirred at ambient temperature for 18 hours. The mixture was basified by the addition of sodium bicarbonate. The mixture was evaporated and the residue was partitioned between ethyl acetate and water. The organic layer was dried (Na$_2$SO$_4$) and evaporated. There was thus obtained 3-[3-(4-acetylphenylthio)-5-fluorophenyl]-3-methoxy-1-(prop-2-ynyl)pyrrolidine (0.048 g, 98%) which was used without further purification.

EXAMPLE 32

Using an analogous procedure to that described in Example 27, 3-[3-(4-acetylphenylthio)-5-fluorophenyl]-3-methoxy-1-(2,2,2-trifluoroethyl)pyrrolidine was reacted with hydroxylamine hydrochloride to give 3-{5-fluoro-3-[4-(1-hydroxyiminoethyl)phenylthio]phenyl}-3-methoxy-1-(2,2,2-trifluoroethyl)pyrrolidine as a gum in 81% yield.

NMR Spectrum (CD$_3$SOCD$_3$) 1.9–2.3 (m, 5H), 2.8–3.15 (m, 7H), 3.35 (m, 2H), 7.0 (m, 1H), 7.05–7.2 (m, 2H), 7.41 (m, 2H), 7.69 (m, 2H), 11.29 (s, 1H).

The 3-[3-(4-acetylphenylthio)-5-fluorophenyl]-3-methoxy-1-(2,2,2-trifluoroethyl)pyrrolidine used as a starting material was obtained as follows:

Using an analogous procedure to that described in the third paragraph of the portion of Example 5 which is concerned with the preparation of starting materials, 3-{5-fluoro-3-[4-(2-methyl-1,3-dioxolan-2-yl)phenylthio]phenyl}-3-methoxypyrrolidine was reacted with ethyl trifluoroacetate to give 3-{5-fluoro-3-[4-(2-methyl-1,3-dioxolan-2-yl)phenylthio]phenyl}-3-methoxy-1-(trifluoroacetyl)pyrrolidine as a gum in 58% yield.

A mixture of the pyrrolidine so obtained (0.19 g), borane-THF complex (1M in THF, 1 ml) and THF (5 ml) was stirred and heated to reflux for 2 hours. The mixture was cooled to ambient temperature and methanol (10 ml) was added. The mixture was evaporated. A mixture of the resultant residue, 2N aqueous hydrochloric acid (1 ml) and acetone (20 ml) was stirred at ambient temperature for 18 hours. The mixture was evaporated and the residue was partitioned between ethyl acetate and water. The organic phase was dried (Na$_2$SO$_4$) and evaporated. The residue was purified by column chromatography using increasingly polar mixtures of hexane and ethyl acetate as eluent. These were thus obtained in turn:

3-(4-acetylphenylthio)-5-fluorophenyl]-3-methoxy-1-(2,2,2-trifluoroethyl)pyrrolidine as a gum (0.056 g, 33%); and 3-{5-fluoro-3-[4-(1-hydroxyethyl)phenylthio]phenyl}-3-methoxy-1-(2,2,2-trifluoroethyl)pyrrolidine as a gum (0.06 g, 35%).

EXAMPLE 33

Using an analogous procedure to that described in Example 3 except that diisopropylethylamine was used in place of potassium carbonate, (2RS,3SR)-3-[3-(1-ethyl-2-oxo-1,2-dihydroquinolin-6-ylmethoxy)phenyl]-3-methoxy-2-methylpyrrolidine was reacted with 2-propynyl bromide to give (2RS,3SR)-3-[3-(1-ethyl-2-oxo-1,2-dihydroquinolin-6-ylmethoxy)phenyl]-3-methoxy-2-methyl-1-(prop-2-ynyl)pyrrolidine as a gum in 50% yield.

NMR Spectrum 1.0 (d, 3H), 1.36 (t, 3H), 2.15 (m, 1H), 2.3–2.6 (m, 3H), 2.86 (m, 1H), 3.1–3.3 (m, 4H), 3.55 (m, 2H), 4.37 (m, 1H), 5.13 (s, 2H), 6.72 (d, 1H), 6.85–7.1 (m, 3H), 7.25–7.45 (m, 2H), 7.6–7.75 (m, 3H).

The (2RS,3SR)-3-[3-(1-ethyl-2-oxo-1,2-dihydroquinolin-6-ylmethoxy)phenyl]-3-methoxy-2-methylpyrrolidine used as a starting material was obtained as follows:

Using an analogous procedure to that described in the portion of Example 1 which is concerned with the preparation of starting materials, 3-benzyloxybromobenzene was reacted with 1-ethoxycarbonyl-2-methylpyrrolidin-3-one (*J. Med. Pharm. Chem.*, 1962, 5, 755) and the resultant product was reacted with methyl iodide to give (2RS,3SR)-3-(3-benzyloxyphenyl)-1-ethoxycarbonyl-3-methoxy-2-methylpyrrolidine in 65% yield as an oil.

Using an analogous procedure to that described in the portion of Example 2 which is concerned with the preparation of starting materials, the pyrrolidine so obtained was hydrolysed to give (2RS,3SR)-3-(3-benzyloxyphenyl)-3-methoxy-2-methylpyrrolidine as a gum in 54% yield.

Using an analogous procedure to that described in the third paragraph of the portion of Example 5 which is concerned with the preparation of starting materials, the pyrrolidine so obtained was reacted with ethyl trifluoroacetate to give (2RS,3SR)-3-(3-benzyloxyphenyl)-3-methoxy-2-methyl-1-(trifluoroacetyl)pyrrolidine as a gum in 61% yield.

Using an analogous procedure to that described in the last paragraph of the portion of Example 5 which is concerned with the preparation of starting materials, the pyrrolidine so obtained was reacted with hydrogen to give (2RS,3SR)-3-(3-hydroxyphenyl}-3-methoxy-2-methyl-1-(trifluoroacetyl)pyrrolidine as a gum in 98% yield.

Using an analogous procedure to that described in Example 5, the pyrrolidine so obtained was reacted with 6-bromomethyl-1-ethyl-1,2-dihydroquinolin-2-one to give (2RS,3SR)-3-[3-(1-ethyl-2-oxo-1,2-dihydroquinolin-6-ylmethoxy)phenyl]-3-methoxy-2-methyl-1-(trifluoroacetyl)pyrrolidine as a gum in 56% yield.

Using an analogous procedure to that described in the last paragraph of the portion of Example 17 which is concerned with the preparation of starting materials, the pyrrolidine so obtained was hydrolysed to give (2RS,3SR)-3-[3-(1-ethyl-2-oxo-1,2-dihydroquinolin-6-ylmethoxy)phenyl]-3-methoxy-2-methylpyrrolidine as a gum in 98% yield.

EXAMPLE 34

The following illustrate representative pharmaceutical dosage forms containing the compound of formula I, or a pharmaceutically-acceptable salt thereof (hereafter compound X), for therapeutic or prophylactic use in humans:

| (a) Tablet I | mg/tablet |
|---|---|
| Compound X | 100 |
| Lactose Ph. Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound X | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
|---|---|
| Compound X | 1.0 |
| Lactose Ph. Eur | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Compound X | 10 |
| Lactose Ph. Eur | 488.5 |
| Magnesium stearate | 1.5 |

| (e) Injection I | (50 mg/ml) |
|---|---|
| Compound X | 5.0% w/v |
| 1 M Sodium hydroxide solution | 15.0% v/v |
| 0.1 M Hydrochloric acid (to adjust pH to 7.6) | |
| Polyethylene glycol 400 | 4.5% w/v |
| Water for injection to 100% | |

| (f) Injection II | (10 mg/ml) |
|---|---|
| Compound X | 1.0% w/v |
| Sodium phosphate BP | 3.6% w/v |
| 0.1 M Sodium hydroxide solution | 15.0% v/v |
| Water for injection to 100% | |

| (g) Injection III | (1 mg/ml, buffered to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

| (h) Aerosol I | mg/ml |
|---|---|
| Compound X | 10.0 |
| Sorbitan trioleate | 13.5 |
| Trichlorofluoromethane | 910.0 |
| Dichlorodifluoromethane | 490.0 |

| (i) Aerosol II | mg/ml |
|---|---|
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

| (j) Aerosol III | mg/ml |
|---|---|
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |

| (k) Aerosol IV | mg/ml |
|---|---|
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

Note
The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

CHEMICAL FORMULAE

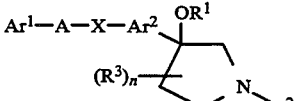

I

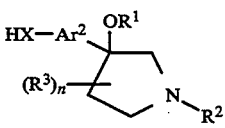

II

-continued
CHEMICAL FORMULAE

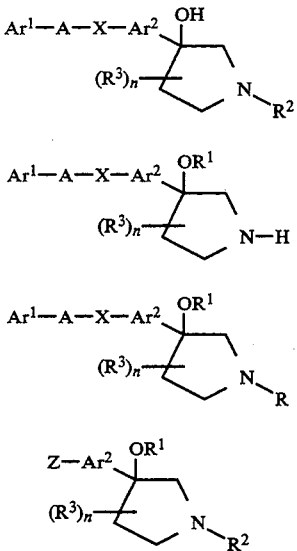

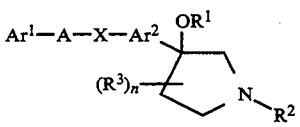

We claim:
1. A pyrrolidine derivative of the formula I

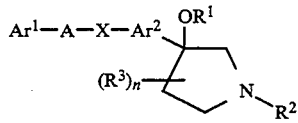

wherein $Ar^1$ is naphthyl or $Ar^1$ is phenyl which bears a substituent selected from hydroxyimino-(1-4C)alkyl, (1-4C)alkoxyimino-(1-4C)-alkyl, (2-5C)alkanoyloxyimino-(1-4C)alkyl, cyano-(1-4C)alkoxyimino-(1-4C)alkyl, hydroxyamino-(1-4C)alkyl, (1-4C)alkoxyamino-(1-4C)-alkyl, N-hydroxyureido-(1-4C)alkyl, N-(1-4C)alkoxyureido-(1-4C)alkyl, N-hydroxy-(2-4C)alkanoylamino-(1-4C)alkyl, N-(1-4C)alkoxy-(2-4C)alkanoylamino-(1-4C)alkyl, (1-6C)alkylideneaminooxy-(1-4C)alkyl, and which phenyl group may optionally bear a further substituent selected from halogeno, (1-4C)alkyl and (1-4C)alkoxy;

A is a direct link to the group X or A is (1-4C)alkylene;

X is oxy, thio, sulphinyl or sulphonyl;

$Ar^2$ is phenylene or thiophendiyl, which may optionally bear one or two substituents selected from halogeno, cyano, trifluoromethyl, hydroxy, amino, (1-4C)alkyl, (1-4C)alkoxy, (1-4C)alkylamino and di-(1-4C)alkylamino;

$R^1$ is hydrogen, (1-4C)alkyl, (3-4C)alkenyl or (3-4C)alkynyl;

$R^2$ is (1-4C)alkyl, (2-4C)alkenyl, (2-4C)alkynyl, halogeno-(1-4C)alkyl, halogeno-(2-4C)alkenyl, halogeno-(2-4C)alkynyl, (1-4C)alkoxy-(2-4C)alkyl, hydroxy-(2-4C)alkyl, cyano-(1-4C)alkyl, carboxy-(1-4C)alkyl, carbamoyl-(1-4C)alkyl, (1-4C)alkoxycarbonyl-(1-4C)alkyl, N-(1-4C)alkylcarbamoyl-(1-4C)alkyl or N,N-di-(1-4C)alkylcarbamoyl-(1-4C)alkyl; and n is 1 or 2, and each $R^3$ is independently hydrogen, hydroxy, (1-4C)alkyl or (1-4C)alkoxy;

or a pharmaceutically-acceptable salt thereof.

2. A pyrrolidine derivative of the formula I wherein $Ar^1$ is naphthyl or $Ar^1$ is phenyl which bears a substituent selected from hydroxyimino-(1-4C)alkyl, (1-4C)alkoxyimino-(1-4C)-alkyl, (2-5C)alkanoyloxyimino-(1-4C)alkyl, cyano-(1-4C)alkoxyimino-(1-4C)alkyl, hydroxyamino-(1-4C)alkyl, (1-4C)alkoxyamino-(1-4C)-alkyl, N-hydroxyureido-(1-4C)alkyl, N-(1-4C)alkoxyureido-(1-4C)alkyl, N-hydroxy-(2-4C)alkanoylamino-(1-4C)alkyl, N-(1-4C)alkoxy-(2-4C)alkanoylamino-(1-4C)alkyl, (1-6C)alkylideneaminooxy-(1-4C)alkyl, and which phenyl group may optionally bear a further substituent selected from halogeno, (1-4C)alkyl and (1-4C)alkoxy;

A is a direct link to the group X or A is (1-4C)alkylene;

X is oxy, thio, sulphinyl or sulphonyl;

$Ar^2$ is phenylene or thiophendiyl, which may optionally bear one or two substituents selected from halogeno, cyano, trifluoromethyl, hydroxy, amino, (1-4C)alkyl, (1-4C)alkoxy, (1-4C)alkylamino and di-(1-4C)alkylamino;

$R^1$ is (1-4C)alkyl, (3-4C)alkenyl or (3-4C)alkynyl;

$R^2$ is (1-4C)alkyl, (2-4C)alkenyl, (2-4C)alkynyl, halogeno-(1-4C)alkyl, halogeno-(2-4C)alkenyl, halogeno-(2-4C)alkynyl, (1-4C)alkoxy-(2-4C)alkyl, hydroxy-(2-4C)alkyl, cyano-(1-4C)alkyl, carboxy-(1-4C)alkyl, carbamoyl-(1-4C)alkyl, (1-4C)alkoxycarbonyl-(1-4C)alkyl, N-(1-4C)alkylcarbamoyl-(1-4C)alkyl or N,N-di-(1-4C)alkylcarbamoyl-(1-4C)alkyl; and n is 1 or 2, and each $R^3$ is independently hydrogen, hydroxy, (1-4C)alkyl or (1-4C)alkoxy;

or a pharmaceutically-acceptable salt thereof.

3. A pyrrolidine derivative of the formula I as claimed in claim 1 or claim 2 wherein Ar is phenyl which bears a substituent selected from hydroxyimino-(1-4C)alkyl, (1-4C)alkoxyimino-(1-4C)alkyl, (2-5C)alkanoyloxyimino-(1-4C)alkyl, cyano-(1-4C)alkoxyimino-(1-4C)alkyl, hydroxyamino-(1-4C)alkyl, (1-4C)alkoxyamino-(1-4C)alkyl, N-hydroxyureido-(1-4C)alkyl, N-(1-4C)alkoxyureido-(1-4C)alkyl, N-hydroxy-(2-4C)alkanoylamino-(1-4C)alkyl, N-(1-4C)alkoxy-(2-4C)alkanoylamino-(1-4C)alkyl and (1-6C)alkylideneaminooxy-(1-4C)alkyl, and $Ar^1$ may optionally bear a further substituent selected from halogeno, (1-4C)alkyl and (1-4C)alkoxy;

A is a direct link to the group X or A is (1-4C)alkylene;

X is oxy, thio, sulphinyl or sulphonyl;

$Ar^2$ is phenylene, or thiophendiyl, which may optionally bear one or two substituents selected from halogeno, cyano, trifluoromethyl, hydroxy, amino, (1-4C)alkyl, (1-4C)alkoxy, (1-4C)alkylamino and di-(1-4C)alkylamino;

$R^1$ is hydrogen, (1-4C)alkyl, (3-4C)alkenyl or (3-4C)alkynyl;

$R^2$ is (1-4C)alkyl, (2-4C)alkenyl, (2-4C)alkynyl, halogeno-(1-4C)alkyl, halogeno-(2-4C)alkenyl, halogeno-(2-4C)alkynyl, (1-4C)alkoxy-(2-4C)alkyl, hydroxy-(2-4C)alkyl, cyano-(1-4C)alkyl, carboxy-(1-4C)alkyl, carbamoyl-(1-4C)alkyl, (1-4C)alkoxycarbonyl-(1-4C)alkyl, N-(1-4C)alkylcarbamoyl- (1-4C)alkyl or N,N-di-(1-4C)alkylcarbamoyl-(1-4C)alkyl; and n is 1 or 2 and each $R^3$ is independently hydrogen, hydroxy, (1-4C)alkyl or (1-4C)alkoxy;

or a pharmaceutically-acceptable salt thereof.

4. A pyrrolidine derivative of the formula I as claimed in claim 1 or claim 2 wherein $Ar^1$ is 4-(1-hydroxyiminoethyl)phenyl or 4-(1-cyanomethoxyiminoethyl)phenyl;

A is a direct link to X and X is thio or sulphonyl;

$Ar^2$ is 1,3-phenylene, 5-fluoro-1,3-phenylene, 2,5-thiophenediyl or 2,4-thiophenediyl (with the group of the formula -A-X- in the 2-position);

$R^1$ is methyl;

$R^2$ is prop-2-ynyl, 2,2-difluoroethyl or 2,2,2-trifluoroethyl;

n is 1 and $R^3$ is hydrogen;

or a pharmaceutically-acceptable salt thereof.

5. A pyrrolidine derivative of the formula I as claimed in claim 1 or claim 2 selected from:

3-{2-[4-(1-hydroxyiminoethyl)phenylthio]thien-4-yl}-3-methoxy-1-(2,2,2-trifluoroethyl)pyrrolidine, 3-{3-[4-(1-cyanomethoxyiminoethyl)phenylthio]phenyl}-3-methoxy-1-(2,2,2-trifluoroethyl)pyrrolidine, 3-{5-fluoro-3-[4-(1-hydroxyiminoethyl)phenylthio]phenyl}-3-methoxy-1-(prop-2-ynyl)pyrrolidine and 3-{5-fluoro-3-[4-(1-hydroxyiminoethyl)phenylthio]phenyl}-3-methoxy-1-(2,2,2-trifluoroethyl)pyrrolidine;

or a pharmaceutically-acceptable salt thereof.

6. A pharmaceutical composition which comprises a pyrrolidine derivative of the formula I, or a pharmaceutically-acceptable salt thereof, as claimed in any one of claims 1 to 2 in association with a pharmaceutically-acceptable diluent or carrier.

7. A method of treating a disease or medical condition mediated by one or more leukotrienes which comprises administering to a warm blooded animal requiring such treatment an effective amount of a pyrrolidine derivative of the formula I, or a pharmaceutically-acceptable salt thereof, as claimed in any one of claims 1 to 2.

8. A pharmaceutical composition which comprises a pyrrolidine derivative of the formula I, or a pharmaceutically-acceptable salt thereof, as claimed in claim 3 in association with a pharmaceutically-acceptable diluent or carrier.

9. A pharmaceutical composition which comprises a pyrrolidine derivative of the formula I, or a pharmaceutically-acceptable salt thereof, as claimed in claim 4 in association with a pharmaceutically-acceptable diluent or carrier.

10. A pharmaceutical composition which comprises a pyrrolidine derivative of the formula I, or a pharmaceutically-acceptable salt thereof, as claimed in claim 5 in association with a pharmaceutically-acceptable diluent or carrier.

11. A method of treating a disease or medical condition mediated by one or more leukotrienes which comprises administering to a warm blooded animal requiring such treatment an effective amount of a pyrrolidine derivative of the formula I, or a pharmaceutically-acceptable salt thereof, as claimed in claim 3.

12. A method of treating a disease or medical condition mediated by one or more leukotrienes which comprises administering to a warm blooded animal requiring such treatment an effective amount of a pyrrolidine derivative of the formula I, or a pharmaceutically-acceptable salt thereof, as claimed in claim 4.

13. A method of treating a disease or medical condition mediated by one or more leukotrienes which comprises administering to a warm blooded animal requiring such treatment an effective amount of a pyrrolidine derivative of the formula I, or a pharmaceutically-acceptable salt thereof, as claimed in claim 5.

* * * * *